(12) United States Patent
Solsberg et al.

(10) Patent No.: US 10,912,605 B2
(45) Date of Patent: Feb. 9, 2021

(54) DEVICES, KITS AND METHODS RELATING TO TREATMENT OF FACET JOINTS

(71) Applicant: Thixos LLC, Greenwood Village, CO (US)

(72) Inventors: Murray David Solsberg, Greenwood Village, CO (US); Douglas Preston Beall, Oklahoma City, OK (US); Ryan Erich Dean, Valhalla, NY (US)

(73) Assignee: Thixos LLC, Greenwood Village, CO (US)

( * ) Notice: Subject to any disclaimer, the term of this patent is extended or adjusted under 35 U.S.C. 154(b) by 0 days.

(21) Appl. No.: 16/271,133

(22) Filed: Feb. 8, 2019

(65) Prior Publication Data

US 2019/0167343 A1 Jun. 6, 2019

Related U.S. Application Data

(62) Division of application No. 15/036,169, filed as application No. PCT/US2014/064925 on Nov. 11, 2014, now Pat. No. 10,238,450.

(Continued)

(51) Int. Cl.
*A61B 18/14* (2006.01)
*A61B 17/34* (2006.01)
(Continued)

(52) U.S. Cl.
CPC ...... *A61B 18/1482* (2013.01); *A61B 17/3417* (2013.01); *A61B 17/3421* (2013.01);
(Continued)

(58) Field of Classification Search
CPC .......... A61B 17/3417; A61B 2217/007; A61B 221/7005; A61B 2017/3454; A61B 18/1482; A61B 18/1206
See application file for complete search history.

(56) References Cited

U.S. PATENT DOCUMENTS 4,074,718 A 2/1978 Morrison, Jr.
4,545,374 A 10/1985 Jacobsen
(Continued)

FOREIGN PATENT DOCUMENTS

EP 0143393 A2 6/1985
EP 1173198 11/2003
(Continued)

OTHER PUBLICATIONS

Martha et al. "Outcome of percutaneous rupture of lumbar synovial cysts: a case series of 101 patients," The Spine Journal 9 (2009) 899-904.

*Primary Examiner* — Ellen C Hammond
*Assistant Examiner* — Tara Rose E Carter
(74) *Attorney, Agent, or Firm* — Snell & Wilmer L.L.P.

(57) ABSTRACT

A facet joint surgical tool for treating a facet joint synovial cyst includes rotatable members disposed side-by-side through a minimally invasive sheath and rotatable to reconfigure distal end portions between a facet joint penetration configuration with a tissue piercing tip and a facet joint retraction configuration. Facet joint synovial cysts located to an anterior side of the facet joint are treated by a posterior approach with access to the cyst through the facet joint retracted by the surgical tool. Facet joint synovial cysts located to a posterior side of the facet joint are treated by direct access from a posterior approach.

19 Claims, 28 Drawing Sheets

Related U.S. Application Data

(60) Provisional application No. 61/903,806, filed on Nov. 13, 2013.

(51) Int. Cl.
*A61B 18/12* (2006.01)
*A61B 17/02* (2006.01)
*A61B 17/32* (2006.01)
*A61B 18/00* (2006.01)

(52) U.S. Cl.
CPC ...... *A61B 18/1206* (2013.01); *A61B 17/3439* (2013.01); *A61B 18/1487* (2013.01); *A61B 2017/0256* (2013.01); *A61B 2017/320044* (2013.01); *A61B 2017/3454* (2013.01); *A61B 2018/00339* (2013.01); *A61B 2018/00577* (2013.01); *A61B 2217/005* (2013.01); *A61B 2217/007* (2013.01)

(56) References Cited

U.S. PATENT DOCUMENTS

| | | |
|---|---|---|
| 4,569,338 A | 2/1986 | Edwards |
| 5,599,345 A | 2/1997 | Edwards et al. |
| 6,014,588 A | 1/2000 | Fitz |
| 6,246,912 B1 | 6/2001 | Sluijter et al. |
| 6,436,102 B1 | 8/2002 | Ralph et al. |
| 6,454,765 B1 | 9/2002 | Leveen et al. |
| 6,478,801 B1 | 11/2002 | Ralph et al. |
| 6,520,967 B1 | 2/2003 | Cauthen |
| 6,558,390 B2 | 5/2003 | Cragg |
| 6,605,085 B1 | 8/2003 | Edwards |
| 6,685,700 B2 | 2/2004 | Behl et al. |
| 6,881,214 B2 | 4/2005 | Cosman et al. |
| 7,001,379 B2 | 2/2006 | Behl et al. |
| 7,226,451 B2 | 1/2007 | Shluzas et al. |
| 7,179,255 B2 | 2/2007 | Lettice et al. |
| 7,207,989 B2 | 4/2007 | Pike, Jr. et al. |
| 7,211,085 B2 | 5/2007 | Michelson |
| 7,294,127 B2 | 11/2007 | Leung et al. |
| 7,309,338 B2 | 12/2007 | Cragg |
| 7,344,533 B2 | 3/2008 | Pearson et al. |
| 7,364,578 B2 | 4/2008 | Francischelli et al. |
| 7,422,587 B2 | 9/2008 | Bek et al. |
| 7,467,075 B2 | 12/2008 | Humphries et al. |
| 7,591,851 B2 | 9/2009 | Winslow et al. |
| 7,601,170 B2 | 10/2009 | Winslow et al. |
| 7,763,050 B2 | 7/2010 | Winslow et al. |
| 7,794,463 B2 | 9/2010 | Cragg |
| 7,799,033 B2 | 9/2010 | Assell et al. |
| 7,837,713 B2 | 11/2010 | Petersen |
| 7,879,031 B2 | 2/2011 | Peterson |
| 7,909,832 B2 | 3/2011 | Michelson |
| 8,021,392 B2 | 9/2011 | Petersen |
| 8,038,717 B2 | 10/2011 | Ralph et al. |
| 8,066,710 B2 | 11/2011 | Estes et al. |
| 8,192,357 B2 | 1/2012 | Miles et al. |
| 8,123,751 B2 | 2/2012 | Shluzas |
| 8,123,786 B2 | 2/2012 | Lins |
| 8,137,404 B2 | 5/2012 | Lopez et al. |
| 8,187,179 B2 | 5/2012 | Miles et al. |
| 8,187,304 B2 | 5/2012 | Malek |
| 8,288,142 B2 | 10/2012 | Uvarkina et al. |
| 8,303,630 B2 | 11/2012 | Abdou |
| 8,337,508 B2 | 12/2012 | Lavallee et al. |
| 8,343,162 B2 | 1/2013 | Ralph et al. |
| 8,409,208 B2 | 4/2013 | Abdou |
| 8,409,257 B2 | 4/2013 | Edidin et al. |
| 2004/0093001 A1 | 5/2004 | Hamada |
| 2005/0025765 A1* | 2/2005 | DiMauro ............ A61K 31/198 424/145.1 |
| 2005/0113824 A1 | 5/2005 | Sartor et al. |
| 2005/0131405 A1 | 6/2005 | Molz, IV et al. |
| 2005/0171551 A1 | 8/2005 | Sukovich et al. |
| 2005/0240264 A1 | 10/2005 | Tokish, Jr. et al. |
| 2006/0095066 A1* | 5/2006 | Chang ................ A61B 17/1204 606/199 |
| 2006/0149373 A1 | 7/2006 | Winslow et al. |
| 2006/0241648 A1 | 10/2006 | Bleigh et al. |
| 2006/0271057 A1 | 11/2006 | Shluzas et al. |
| 2007/0055271 A1 | 3/2007 | Schaller |
| 2007/0055272 A1 | 3/2007 | Schaller |
| 2007/0055273 A1 | 3/2007 | Schaller |
| 2007/0083200 A1 | 4/2007 | Gittings et al. |
| 2007/0083266 A1 | 4/2007 | Lang |
| 2007/0185490 A1 | 8/2007 | Implicito |
| 2007/0233244 A1 | 10/2007 | Lopez et al. |
| 2007/0233261 A1 | 10/2007 | Lopez et al. |
| 2007/0260240 A1 | 11/2007 | Rusin |
| 2007/0282449 A1 | 12/2007 | De Villiers et al. |
| 2008/0097441 A1 | 4/2008 | Hayes et al. |
| 2008/0234827 A1 | 9/2008 | Schaller et al. |
| 2009/0017058 A1 | 1/2009 | Arad et al. |
| 2009/0112264 A1 | 4/2009 | Lins |
| 2009/0131986 A1 | 5/2009 | Lee et al. |
| 2009/0138053 A1 | 5/2009 | Assell et al. |
| 2009/0177205 A1 | 7/2009 | McCormack et al. |
| 2009/0182386 A1 | 7/2009 | Schaller |
| 2009/0204152 A1* | 8/2009 | Blain ................ A61B 17/88 606/249 |
| 2009/0216234 A1 | 8/2009 | Farr et al. |
| 2009/0292316 A1 | 11/2009 | Hess |
| 2009/0306671 A1 | 12/2009 | McCormack et al. |
| 2009/0312763 A1 | 12/2009 | McCormack et al. |
| 2009/0312807 A1 | 12/2009 | Boudreault et al. |
| 2010/0069912 A1 | 3/2010 | McCormack et al. |
| 2010/0191241 A1 | 7/2010 | McCormack et al. |
| 2010/0331780 A1 | 12/2010 | Bellisario et al. |
| 2011/0054530 A1 | 3/2011 | Lins |
| 2011/0098531 A1 | 4/2011 | To |
| 2011/0230965 A1 | 9/2011 | Schell et al. |
| 2012/0035727 A1 | 2/2012 | Lins |
| 2012/0083662 A1 | 4/2012 | Hamada et al. |
| 2012/0116454 A1 | 5/2012 | Edidin et al. |
| 2012/0232658 A1 | 9/2012 | Morgenstern et al. |
| 2012/0266699 A1 | 10/2012 | Brandt et al. |
| 2012/0303034 A1 | 11/2012 | Woolley et al. |
| 2012/0308510 A1 | 12/2012 | Laico |
| 2013/0006364 A1 | 1/2013 | McCormack et al. |
| 2013/0053851 A1 | 2/2013 | Schmitz et al. |
| 2013/0131444 A1 | 5/2013 | Boudreault et al. |

FOREIGN PATENT DOCUMENTS

| | | |
|---|---|---|
| EP | 1645235 | 4/2006 |
| EP | 1957088 | 11/2010 |
| EP | 2520255 | 11/2012 |

* cited by examiner

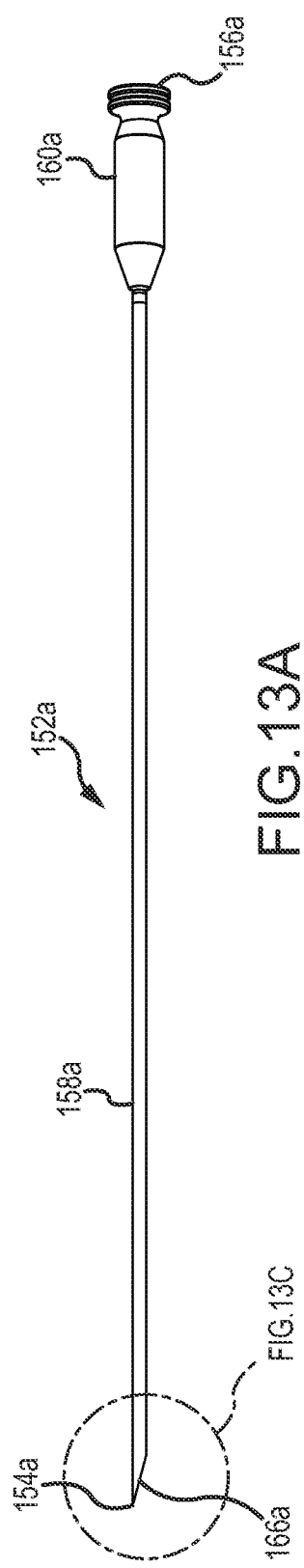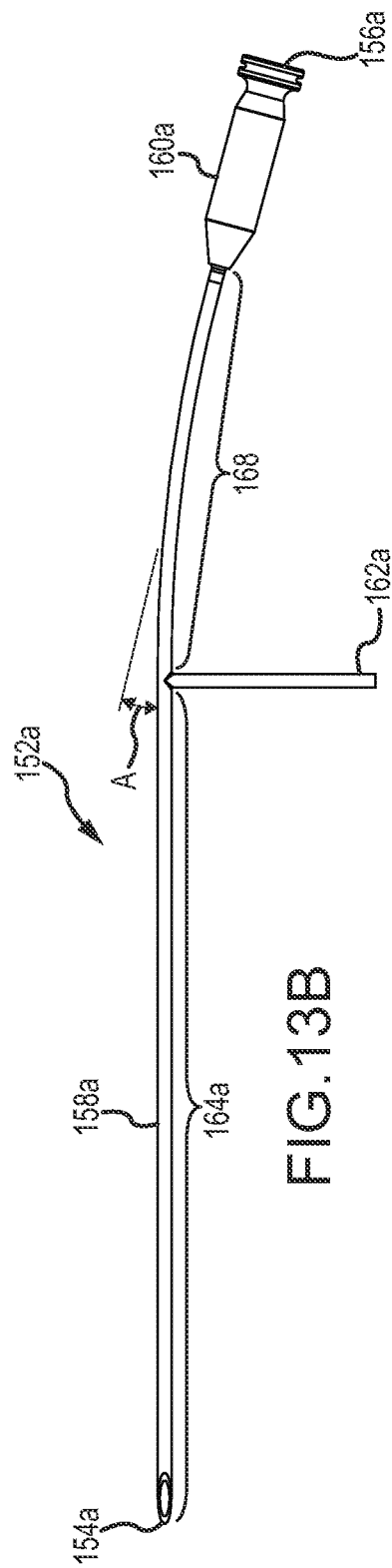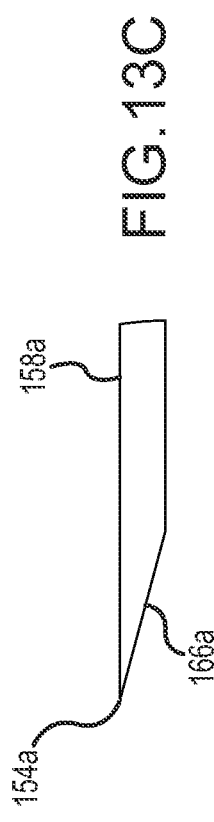
FIG.13A
FIG.13B
FIG.13C

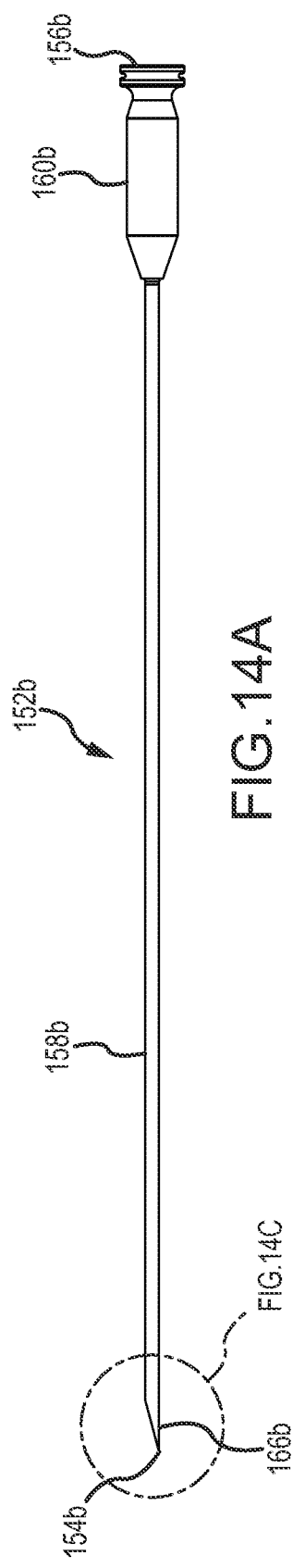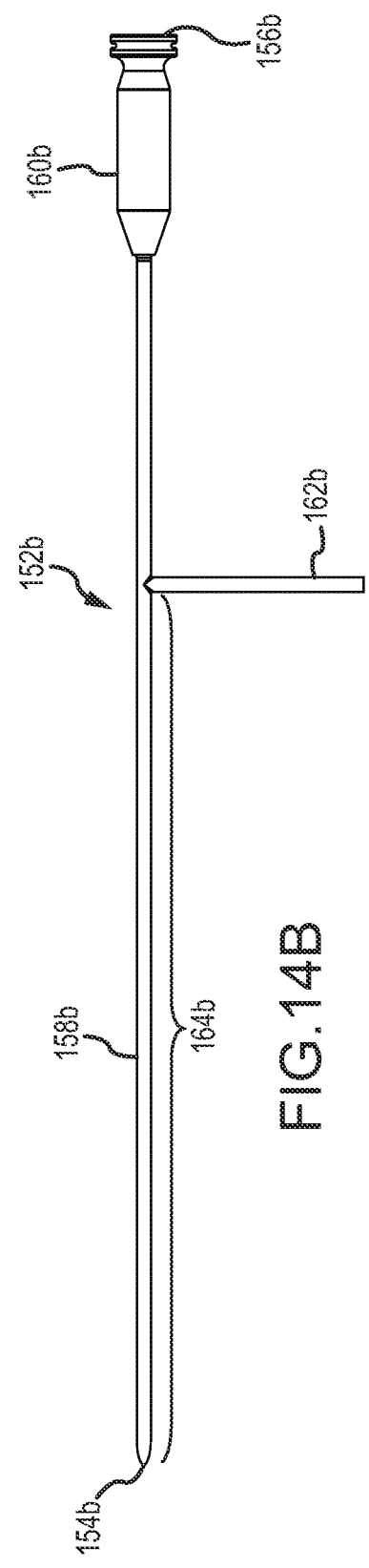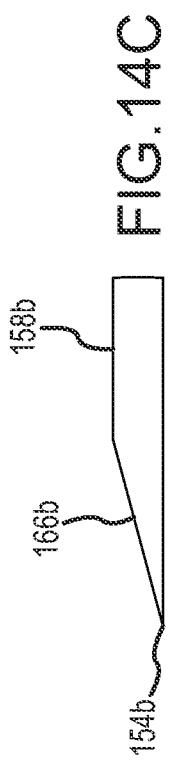

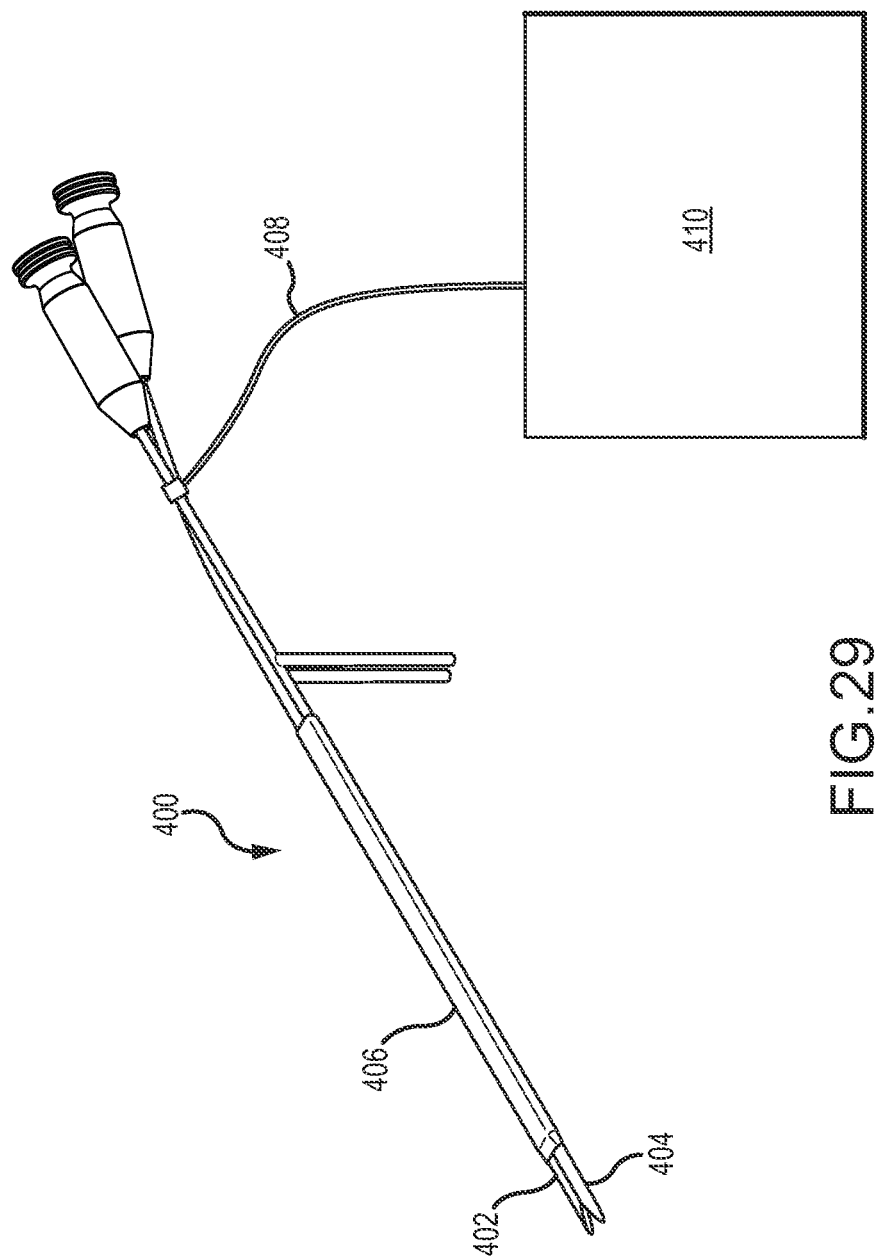

DEVICES, KITS AND METHODS RELATING TO TREATMENT OF FACET JOINTS

CROSS-REFERENCE TO RELATED APPLICATIONS

This application is a divisional of prior non-provisional U.S. patent application Ser. No. 15/036,169, filed May 12, 2016, entitled "DEVICES, KITS AND METHODS RELATING TO TREATMENT OF FACET JOINTS", which is a national stage of PCT Application PCT/US2014/064925, entitled "DEVICES, KITS AND METHODS RELATING TO TREATMENT OF FACET JOINTS", filed Nov. 11, 2014, which in turn claims benefit of U.S. provisional patent application No. 61/903,806 entitled "DEVICES, KITS AND METHODS RELATING TO TREATMENT OF FACET JOINTS" filed Nov. 13, 2013, all of which are incorporated herein by reference.

FIELD OF INVENTION

This invention relates to the spine and facet joints, including with respect to minimally invasive procedures to treat facet joint synovial cysts, which may be image guided.

BACKGROUND OF INVENTION

Back pain is the commonest cause of disability. Approximately 40% of back pain is caused by disorders of the facet joints.

The facet joints (also called zygapophysial joints or z-joints) are paired structures on the back and side of the spine. These joints support the torso during flexion, extension and rotation of the spine. These are synovial joints and therefore contain joint fluid. Joint fluid is viscous and a lubricant. Synovial cysts occur along the margins of many joints in the body. These cysts are caused by a degenerative process. Synovial cysts are lined by synovial cells.

These cysts frequently occur along the margins of the facet joint. These cysts may occur on the back (posterior) or the front (anterior) of the facet joints. The sensitive nerve structures are located on the front of the joint and therefore anterior cysts located within the spinal canal are usually symptomatic. Cysts along the back of the joints may be associated with back pain but are usually asymptomatic. When there is a cyst on the back of the joint there is usually no anterior cyst present. This is believed to be due to relative decompression of the anterior joint capsule pressure into the posterior capsule.

When these cysts enlarge into the spinal canal they cause back pain and/or radiculopathy (leg pain) by compressing the adjacent structures and nerves. These benign cysts usually are connected to the adjacent joint. In the spine these cysts usually arise from the facet joints but also may occur within the spinal ligaments rarely.

Fluid, bone, cartilage fragments and debris are frequently present in arthritic joints. Synovial cysts arise from arthritic joints.

The current treatment of synovial cysts is usually surgical. During the surgical procedure an incision is made in the back and the muscles and ligaments are cut and retracted to access the back of the spinal canal. The lamina or back of the bony spinal canal is then removed in order to access the cyst. Then the cyst is surgically removed using a scalpel, cautery or other cutting instruments. The surgical procedure is effective resulting in improvement in leg pain in the majority of patients. However surgery damages surrounding tissues, ligaments and muscles. Also surgery can result in disability due to removal of or damage to the muscle, ligaments and bony structures that mechanically support the spine and may result in spinal instability. Although surgery is usually successful cysts may recur even after a successful operation. A current trend in spinal surgery and intervention is toward tools and techniques to minimize tissue damage using image guidance and minimally invasive techniques Percutaneous aspiration is also used to treat synovial cysts, and in particular synovial cysts located anterior to a facet joint. Instead of directly removing the cyst the joint is aspirated with a needle. Synovial fluid is very thick and often cannot be aspirated using a standard spinal needle. The results of current percutaneous methods of treatment are sub-optimal. Less than half of patients are successfully treated. Also, even when successfully aspirated the cysts may refill with joint fluid resulting in recurrence of symptoms. Therefore many percutaneous aspirations fail to resolve the patient's symptoms and patients often have to undergo a second open surgical procedure to definitively treat their pain with additional risks, expense, recovery time and pain. Direct percutaneous aspiration has traditionally not been an option for synovial cysts located anterior to facet joints.

Percutaneous ablation is used to treat facet related pain but is not used to treat facet cysts. A common method to treat facet related pain is radiofrequency ablation. The nerves supplying the facet joint are heated and this disrupts the nerve function and conduction resulting in pain relief. Also the capsule may be treated directly for treating pain. Radiofrequency energy delivered by a needle or probe is usually used for ablation although cooled probes (cryotherapy), focused ultrasound and alcohol may also be used.

There is a need for percutaneous minimally invasive devices and procedures to access the facet joint and perform various procedures in relation to the facet joint, for example to aspirate thick synovial fluid and definitively treat synovial cysts of the facet joints.

SUMMARY OF INVENTION

Various aspects of the invention are disclosed herein. Disclosed are tools, kits, methods and systems to access the facet joint and to permit medical procedures to be performed in the vicinity of the facet joint, for example to treat facet joint synovial cysts. Methods are disclosed for delivery of tools and medications into the facet joint. Methods and techniques are disclosed to liquefy thick fluids in order to aspirate viscid material through a small tube. This is similar to developing a method to suck oatmeal up a small soda straw. Methods and tools are disclosed for irrigation of joints and which facilitate aspiration of debris and thick fluid from a facet joint. Tools and methods are disclosed to deliver radiofrequency energy to the facet joint, nerves and/or capsule and/or to the wall of synovial cysts of the facet joint. Methods and tools are disclosed to decompress the joint fluid and therefore a connected cyst by making an opening in the back of the facet joint and creating an artificial posterior cyst-like cavity or reservoir for the joint fluid on the back of the joint. Methods are disclosed for ablating the synovial lining of the facet joint and cyst to reduce synovial fluid production and therefore reduce the recurrence of the cyst after either percutaneous treatment or open surgery. Methods are disclosed for reducing scarring and adhesions around facet joints. Methods are disclosed to reduce recurrence of facet cysts after treatment. Methods are disclosed that may be used to drain thick fluids through small tubes in other applications. Devices are disclosed that may be used for treating facet related back pain. Devices are disclosed that may be used before, during or after open surgery to reduce the risk of recurrence of the synovial cyst. Devices and methods are disclosed that may be used to ablate the synovium and capsule of joints.

Although the main focus of the disclosure is to treat spinal cysts adjacent to facet joints the disclosed subject matters and accompanying techniques may also be used to treat cysts around other joints (other synovial joints). As used herein the term "cyst" includes true cysts and also cyst-like occurrences, such as pseudocysts. Moreover, the methods, kits and tools disclosed herein may be used to treat other tissue conditions adjacent to facet joints, and in particular tissue conditions located to an anterior side of a facet joint. True synovial cysts are also referred to as ganglion cysts.

One aspect of this disclosure concerns a facet joint surgical tool. The facet joint surgical tool may include:

a proximal portion to be disposed outside of a patient during a facet joint surgical procedure;

a distal portion to be disposed inside a patient during a facet joint surgical procedure;

a first rotatable member comprising a first distal end portion having a first distal tip, with the first rotatable member being rotatable about a first axis;

a second rotatable member comprising a second distal end portion having a second distal tip, with the second rotatable member being rotatable about a second axis, which second axis is different than the first axis; and the first and second rotatable members are rotatable relative to each other about the first axis and the second axis respectively to manipulate the relative positioning of the first and second distal end portions between a facet joint penetration configuration (also called a piercing configuration) in which the first and second distal end portions are positioned form of piercing tip to pierce through tissue and penetrate into the facet joint and a facet joint retraction configuration in which the first and second distal end portions are positioned to retract the facet joint following penetration into the facet joint.

A number of feature refinements and additional features are applicable to this facet joint surgical tool aspect of the disclosure. These feature refinements and additional features may be used individually or in any combination. As such, any of the following features may be, but are not required to be, used with any other feature or combination of features of this aspect or any other aspect of the disclosure.

The distal portion of one or both of the rotatable members may include a beveled end (e.g., a slanted taper). Such a beveled end, may, for example be a beveled end of a medical needle, such as a spinal needle or hypodermic needle. Such a distal portion may be beveled at an appropriate angle for forming a piercing tip when in the facet joint penetration configuration. The angle of the bevel, being the included angle between a bevel face and the adjoining external wall of the member, may often be in a range having an upper limit of 25°, or 20° and a lower limit of 10° or 15°. A bevel angle in a range of from 17° to 19° may be advantageous for some implementations. One or both of the rotatable members may be hollow, having a lumen, or passage, therethrough. When the rotatable members are in the facet joint penetration configuration, the distal tips of the distal portions of the members may be adjoining and when the rotatable members are in the facet joint retraction configuration such distal tips may be separated by a separation distance for retraction, or widening, of the facet joint. Such a separation distance of the distal tips may be at least 0.5 millimeter, 1 millimeter, 1.5 millimeter, 2 millimeters, 2.5 millimeters or 3 millimeters. Such a separation distance may be not greater than 6.5 millimeters, 5 millimeters, 4 millimeters, 3.5 millimeters or 3 millimeters. When the rotatable members are in the facet joint retraction configuration, the rotatable members may each be rotated by some amount relative to positioning in the facet joint penetration configuration. Such amount may be or be approximately 180° or may be an amount that is less than or more than 180°. The respective axis of each rotatable member may be a central longitudinal axis of that member or a portion thereof. Such longitudinal axes of the members or portions thereof may be parallel or substantially parallel. The rotatable members may be in external tangential contact for at least some longitudinal portion of each rotatable member (e.g., adjoining tubes of circular cross-section in a parallel side-by-side arrangement).

Each of the rotatable members may include a longitudinally extending insertion portion configured for insertion into the body during a surgical operation. Such an insertion portion may have a substantially uniform insertion cross-section between a proximal end of the insertion portion and the distal portion of the rotatable member (e.g., a tubular insertion portion having a uniform circular cross-section). A rotatable member may have a total length that is longer than the insertion portion, for example a non-insertion portion that is to remain outside of the body and which may be manipulated by a medical practitioner during a surgical procedure. Some or all of such a non-insertion may have a cross-section that is the same as an insertion cross-section of the insertion portion. The insertion portion of a rotatable member may have a longitudinal length of at least 20 millimeters, 30 millimeters, 40 millimeters or 50 millimeters. Such a longitudinal length may be no larger than 200 millimeters, 150 millimeters or 100 millimeters. The insertion portion of a rotatable member may have a maximum cross dimension (e.g., diameter of a circular cross-section or major axis of an elliptical cross-section) perpendicular to the respective axis of rotation of the member, of no larger than 3.25 millimeters, 2.5 millimeters, 2 millimeters, 1.75 millimeters or 1.5 millimeters. Such a maximum cross dimension may be at least 0.25 millimeter, 0.5 millimeter, 0.75 millimeter, 1 millimeter, 1.25 millimeters or 1.5 millimeters. The rotatable members, or the insertion portion thereof, may be made of any suitable material, for example stainless steel or other metallic material. The rotatable members may be fabricated from hypotubes.

The insertion portion of a rotatable member may have a longitudinally-extending lumen, or passage, therethrough to provide access from outside of the body to the inside of the body during a surgical procedure. Such a lumen may have a maximum cross dimension (e.g., diameter of a circular cross-section or major axis of an elliptical cross-section) of at least 0.05 millimeter, 0.1 millimeter, 0.25 millimeter, 0.5 millimeter, 0.75 millimeter or 1 millimeter. Such a maximum cross dimension of the lumen may be no larger than 2.5 millimeters, 2 millimeters, 1.5 millimeters or 1.25 millimeters. Such a lumen may have a longitudinal length of at least 10 millimeters, 20 millimeters or 30 millimeters. The longitudinal length of such a lumen may extend for at least the entire longitudinal length of the insertion portion of the rotatable member. The lumen may extend from a proximal portion of the rotatable member to the distal portion of the member. The lumen may have a circular cross-section or may have a different shaped cross-section. The lumen may have a cross-section that is substantially the same over the entire length of the lumen or may have a varying cross-section.

A lumen of one or both of the rotatable members may be fluidly connected with a respective fluid connection hub that is connectable with a fluid manipulation device, such as for example a syringe, to perform a fluid manipulation. Such a fluid manipulation may include aspiration of fluid through the lumen from a distal end of the lumen corresponding with a distal end portion of the rotatable member. Such a fluid manipulation may include injecting fluid through the lumen and out of the distal end of the lumen corresponding with the distal end portion of the corresponding rotatable member. The fluid connection hub may include a luer connector for connecting with a corresponding luer connector on the fluid manipulation device. The fluid manipulation device may include a fluid containment vessel that is fluidly connected a lumen when the fluid manipulation device is connected with the fluid connection hub. The fluid containment vessel may, for example, be provided by a syringe barrel, and may contain a fluid composition for use in performing a medical procedure in the vicinity of a facet joint, for example for treatment of a facet joint synovial cyst. Such a fluid composition may be in the form of an aqueous irrigation liquid, for example a saline solution. Such a fluid composition may include an active component for treatment of a synovial cyst. Such an active component may be effective to liquefy or decompose (e.g., digest) tissue within a synovial cyst. Such an active component may include a hyaluronidase to liquefy tissue within the synovial cyst (e.g., through enzymatic activity). By "liquefy" it is meant that the viscosity of the tissue is reduced, and preferably to an extent that it may be aspirated though a lumen of at least one of the rotatable members. Such an active component may include a collagenase, which may be effective to decompose the tissue through enzymatic digestion. The digested tissue may be left in the synovial cyst to be removed by normal metabolic processes. Alternatively, after some wait period, the digested tissue may become more liquefied and may be aspirated for removal. A concentration of hyaluronidase or collagenase in a fluid composition, typically an aqueous liquid composition, may be in any useful amount to provide some level of liquification or tissue decomposition. Some example concentrations a for hyaluronidase are in a range of from 50 to 300 USP (United States Pharmacopeia) units per milliliter and for a bacterial derived collagenase are in a range of from 0.1 to 0.5 milligrams per milliliter. Treatment of a synovial cyst to remove tissue to decompress the cyst may include multiple cycles of injecting a fluid composition with such an active agent followed by aspiration, until adequate tissue has been removed to affect a desired level of cyst decompression.

One or both of the rotating members may be configured to receive a stylet through a lumen through the rotatable member. When the rotatable members are in the facet joint penetration configuration, such stylets may be received within hollow rotatable members so that the piercing tip pierces through tissue without coring that tissue, which could plug passages through the rotatable members and interfere with subsequent procedures that might be performed through such passages.

Such a stylet may have a beveled tip that corresponds with a beveled distal tip of the corresponding rotatable member. The stylet may be configured so that when fully inserted through the rotatable member, the distal tip of the stylet aligns with the distal tip of the rotatable member to form a uniform penetrating tip, with the distal end of the stylet blocking the distal end of the lumen to prevent coring of tissue.

The rotatable members may include or be operatively connected with structures or devices that are manipulable by a medical practitioner to rotate the rotatable members. Such structures or devices may include handles or levers that are hand manipulable by the medical practitioner to effect relative rotation of the rotatable members. Such structures or devices may include an automated assembly that is actuatable to automatically adjust repositioning of the rotatable members between the facet joint penetration configuration and the facet joint retraction configuration.

The facet joint surgical tool may include a rotation actuation handle connected with each of the rotatable members and each such rotation actuation handle may be hand manipulable to rotate the respective rotatable member about its access of rotation to rotationally reposition the rotatable member, for example from a facet joint penetration configuration to a facet joint retraction configuration. With the rotatable members conterminous at a distal end, the locations of connection of the rotation actuation handles may be at corresponding longitudinal locations along the rotatable members, or may be at offset locations so that the handles do not come together when rotated. Such a rotation actuation handle may project laterally from the rotatable member to which it is connected to only one side of the access of the rotatable members, for example to prevent interference with the adjacent rotatable member. Such rotation actuation handles may typically be disposed proximal of an insertion portion of the rotatable member. Such rotation actuation members may typically be disposed proximal of a proximal end of a sheath when distal portions of the rotatable members are received through the sheath that constrains the rotatable members in a side-by-side relationship during performance of a surgical procedure. Such a rotation actuation handle may be connected to a rotatable member distal to a distal end of an arcuate portion when the rotatable member includes an arcuate portion.

One or both of the rotatable members may include a feature to enhance utility of the rotatable members during a surgical procedure, for example to reduce interference between proximal ends during rotation and to improve accessibility at proximal ends of the rotatable members. In some implementations, one of both of the rotatable members may include an arcuate portion, which may alternatively be referred to as a bent or curved portion. Such an arcuate portion may be beneficially located on a non-insertable portion of the rotatable member, for example proximal of a rotation actuation handle. Such an arcuate portion may provide some separation distance between proximal ends of the rotatable members to enhance accessibility and to reduce interference between the proximal ends of the rotatable members during rotation. Such an arcuate portion may preferably have a bend, or curve, that is not so sharp as to create a significant impairment to fluid flow through a lumen of the rotatable member or insertion of a stylet or insertable surgical tools through the lumen. In some implementations, such an arcuate portion may have a radius of curvature of at least 5 centimeters, at least 10 centimeters or at least 15 centimeters. Such a radius of curvature may often be not larger than 30 centimeters, not larger than 25 centimeters or not larger than 20 centimeters. A rotatable member including such an arcuate portion may include a first longitudinal axis of a first longitudinal portion of the rotatable member located distal of the arcuate portion and a second longitudinal axis of a second longitudinal portion of the rotatable member located proximal of the arcuate portion, and the first longitudinal axis and the second longitudinal axis may intersect with an acute angle of intersection between them that may be at least 3°, at least 5°, at least 10°, at least 12° or at least 15°. Such an angle of intersection may be not larger than 60°, not larger than 45°, not larger than 30°, not larger than 25° or not larger than 20°. When an arcuate portion extends all of the way to a proximal end of the rotatable member, such a second longitudinal axis may be a line tangent to the curve of the arcuate portion at the proximal end. Such an arcuate portion may have any convenient length, and may often have a length, as measured along the curve of the arcuate portion, of at least 10 millimeters, at least 20 millimeters, at least 30 millimeters or at least 40 millimeters. Such a length of the arcuate portion may often be not larger than 150 millimeters, not larger than 100 millimeters, not larger than 75 millimeters, or not larger than 60 millimeters. A distal end of the arcuate portion may be located a significant distance from the distal tip of the rotatable members. Such a distance from the distal tip may be at least 20 millimeters, at least 40 millimeters, at least 60 millimeters, or at least 80 millimeters. Such a distance may often be not more than 250 millimeters, not more than 200 millimeters or not more than 150 millimeters.

The facet joint surgical tool may include a sheath having an internal passage through which the rotatable members are disposed with at least the distal tips of the members being disposed or able to be disposed distal to a distal end of the sheath. The internal passage may have a minimum area cross-section through which the rotatable members are disposed, and such a minimum area cross-section may have an aspect ratio of at least 1.25:1, 1.5:1 or 1.75:1. The aspect ratio may be no larger than 3:1, 2.5:1 or 2.25:1. An aspect ratio of an area (e.g. minimum cross-section) refers to a ratio of the maximum cross dimension of the area (length dimension of the area) to a width dimension that is a maximum cross dimension of the area perpendicular to the length dimension (e.g., for an ellipse a ratio of the major axis to the minor axis). The minimum area cross-section may have an oval shape. Such a minimum area cross-section may have a maximum cross dimension (e.g., major axis of an elliptical cross-section) of at least 0.5 millimeter, 1 millimeter, 1.5 millimeters, 2 millimeters, 2.5 millimeters or 3 millimeters. Such a maximum cross dimension may be no larger than 6.5 millimeters, 5 millimeters, 4 millimeters, 3.5 millimeters or 3 millimeters. The minimum area cross-section may be configured to maintain, or constrain, the rotatable members in a side-by-side orientation through the minimum cross-section, or even through the entire internal passage of the sheath. In such a side-by-side orientation the rotatable members may be translatable through the minimum area cross-section of the sheath in a longitudinal direction through the internal passage but may be substantially not translatable within the minimum area cross-section in a lateral direction, perpendicular to such longitudinal direction. When such rotatable members are in such a side-by-side orientation, a clearance fit between the rotatable members and the sheath may be no larger than 0.5 millimeter, 0.3 millimeter, 0.2 millimeter or 0.1 millimeter. By a clearance fit of a structure or structures received in a receiving structure, it is meant that the received structure or structures (e.g., the rotatable members) as properly received (e.g., in the sheath) may move laterally within the receiving structure perpendicular to a direction of insertion of the received structure or structures into the receiving structure by no more than that amount. The internal passage of the sheath may have a cross-section that is equal to the minimum area cross-section for at least 1 millimeter, 5 millimeters, 10 millimeters or 20 millimeters along the length of the internal passage. The internal passage of the sheath may have a cross-section that is equal to the minimum area cross-section for substantially the entire length of the internal passage. The rotatable members as disposed through the sheath may be such that their respective longitudinal axes do not cross or intersect within the internal passage. Such axis may be parallel through the internal passage of the sheath.

The sheath may have a longitudinally extending insertion portion for insertion into a patient's body during a surgical operation. The insertion portion of the sheath may have a longitudinal length of 10 millimeters, 20 millimeters or 30 millimeters. Such an insertion portion of the sheath may have a longitudinal length of no greater than 200 millimeters, no greater than 150 millimeters or no greater than 100 millimeters. The insertion portion of the sheath may have an insertion cross-section with an aspect ratio as described previously for the minimum cross-section of the internal passage of the sheath. For example, the insertion cross-section may have an aspect ratio of at least 1.25:1, 1.5:1 or 1.75:1. The insertion cross-section may have an aspect ratio of no larger than 3:1, no larger than 2.5:1 or no larger than 2.25:1. The insertion cross-section of the sheath may have a maximum cross dimension (e.g., diameter for a circular cross-section, major axis for an elliptical cross-section) of no larger than 8 millimeters, 6 millimeters, 5 millimeters, 4.5 millimeters, 4 millimeters or 3.5 millimeters. Such a maximum cross dimension may be at least 0.7 millimeter, 1.25 millimeters, 1.75 millimeters, 2.25 millimeters, 2.75 millimeters, 3.25 millimeters or 3.5 millimeters. The insertion cross-section of an insertable structure (e.g., the sheath) identifies a minimum area perpendicular to a direction of insertion through which the insertable structure is able to pass during insertion. The insertion portion of the sheath may have an insertion cross-section that has an oval shape, for example corresponding with an oval shape of the internal passage through the sheath. The sheath may have a substantially uniform cross-section over the entire length of the insertion portion of the sheath (e.g., a uniform oval cross-section). The sheath may have a non-insertion portion that is to remain outside of a patient's body during use, and through which the rotatable members are insertable for insertion into the body. The non-insertion portion of the sheath may have a cross-section that is the same as a cross-section of the insertion portion of the sheath.

The sheath may advantageously have a tapered distal end portion, wherein an exterior cross-section of the sheath tapers to a smaller size moving toward the distal end of the sheath. Such a tapered distal end portion of the sheath facilitates clean penetration of tissue when the facet joint surgical tool is configured to pierce through tissue to access a facet joint. The exterior cross-section taper may be accomplished through gradually reducing the wall thickness of the sheath on the distal end portion of the sheath, for example by grinding off a portion of the wall thickness from a portion of the sheath adjacent the distal end. In preferred implementations, an internal passage through the sheath does not taper to a smaller size in the tapered distal end portion of the sheath. Such a tapered distal end portion may extend from the distal end of the sheath to a location that may be at least 1 millimeter, at least 1.5 millimeters, at least 2 millimeters or at least 2.5 millimeters. Such a tapered distal end portion of the sheath may begin at a location not more than 10 millimeters, not more than 7 millimeters, not more than 5 millimeters, not more than 4 millimeters or not more than 3 millimeters from the distal end of the sheath.

The sheath may have walls made of an electrically conductive material, such as a metallic material (e.g., stainless steel) when one or more components of the facet joint surgical tool is to be used to transmit radio frequency (RF) energy for performing a RF ablation procedure to ablate tissue during a surgical operation, the sheath may include an electrically insulating coating or covering over the exterior surface of some or all of the sheath, to prevent RF energy from being transmitted laterally to tissue not targeted for ablation. Such an electrically insulating covering may be of a plastic, or polymeric, composition, for example including a polyolefin material (e.g., polyethylene, polypropylene, ethylene-propylene copolymers).

When the facet joint surgical tool is to be used to perform a RF ablation procedure using one or more components of the facet joint surgical tool to transmit the RF energy to the tissue to be ablated, the RF energy may be transmitted through one or both of the rotatable members or through the sheath. A RF signal generator may be connected, for example, with one or both of the rotatable members. The connection may be made at a proximal location that is proximal of the sheath when distal portions of the rotatable members are disposed through the sheath during a surgical procedure.

The facet joint surgical tool of this aspect may be or have features of a rotatable blade access device (Rbad) as described below in the Detailed Description section, or may otherwise have features disclosed in the Detailed Description section.

Another aspect of this disclosure concerns a kit that is useful in performance of a medical procedure in the vicinity of a facet joint. The kit includes at least components assembled or assemblable into a facet joint surgical tool, or a subassembly of such a facet joint surgical tool, such as for example according to the facet joint surgical tool aspect of the disclosure. In that regard, the kit may include a first rotatable member, a second rotatable member and a sheath, which as provided in the kit may be either assembled or assemblable into the facet joint surgical tool, or subassembly thereof, of the facet joint surgical tool aspect of the disclosure.

A number of feature refinements and additional features are applicable to this kit aspect of the disclosure. These feature refinements and additional features may be used individually or in any combination. As such, each of the following features may be, but are not required to be, used with any other feature or combinations of features of this kit aspect or any other aspect of the disclosure.

A first rotatable member, second rotatable member and sheath of the kit may be or have any feature or combination of features described with respect to the facet joint surgical tool of the facet joint surgical tool aspect of this disclosure.

The kit may include one or more other components in addition to the rotatable members and the sheath. The kit may include any component or components described in relation to the facet joint surgical tool aspect of the disclosure.

The kit may include at least one fluid composition for use in performing a medical procedure in the vicinity of a facet joint using one or more components of a facet joint surgical tool of the kit. As used herein, in the vicinity of the facet joint refers to in the facet joint or near the facet joint. Such a fluid composition may comprise an irrigation liquid. Such a fluid composition may comprise a drug (active component) for treating a condition in the vicinity of the facet joint, for example to treat for a synovial cyst. Such a fluid composition may include a hyaluronidase. Such a fluid composition may include a collagenase. Such a fluid composition may be provided in a fluid container. Such a fluid composition may be provided in a syringe prefilled with the fluid composition.

Such a fluid composition may be irrigation liquid. Such a fluid composition may be or have any feature of features as described with respect to the facet joint surgical tool aspect of the disclosure. The kit may include multiple fluid compositions for different uses (e.g., irrigation liquid and active component formulation), and the kit may include multiple fluid containers (e.g., multiple pre-filled syringes) containing different fluid compositions. The kit may include multiple fluid containers (e.g., multiple pre-filled syringes) that each contain the same fluid composition, such as may be useful for performing a procedure multiple times using different volumes of the fluid composition (e.g., multiple treatments with hyaluronidase or collagenase).

Yet another aspect of this disclosure concerns a method for performing a medical procedure in the vicinity of the facet joint, and such a method may include using a facet joint surgical tool, such as according to the facet joint surgical tool aspect of the disclosure or as may be provided by the kit aspect of the disclosure.

A number of feature refinements and additional features are applicable to this method aspect. These feature refinements and additional features may be used individually or in any combination. As such, each of the following features may be, but are not required to be, used with any other feature or combination of features of this method aspect or other aspects of this disclosure.

The facet joint surgical tool may be used to treat facet joint synovial cysts, including such cysts located to an anterior side of facet joints and, such cysts located to a posterior side of facet joints. The facet joint surgical tool will typically be inserted through tissue of a patient to access the vicinity of a facet joint from a posterior side of the facet joint. The piercing and retraction features of the facet joint surgical tool may be used to enter and retract a facet joint to provide access through the facet joint for treatment of a synovial cyst located to an anterior side of the facet joint. The facet joint surgical tool may be used to directly access a synovial cyst located to the posterior side of a facet joint, for example to pierce through tissue to the synovial cyst and to pierce into the synovial cyst to perform a medical procedure in relation to the posterior synovial cyst.

A method for treating a tissue condition in or anterior to a facet joint may include accessing and retracting the facet joint from a posterior side opposite the synovial cyst; and with the facet joint retracted, performing a medical procedure from the posterior side through the retracted facet joint to treat tissue in or anterior to the facet joint. The tissue condition may be a synovial cyst, which may be anterior to the facet joint. The medical procedure may include any procedure described with respect to the facet joint surgical tool aspect of the disclosure or the kit aspect of the disclosure. The medical procedure may include applying suction to the facet joint or directly to a synovial cyst or other tissue for aspiration of fluid. The medical procedure may include injecting a fluid composition into the facet joint to apply fluid pressure to a synovial cyst or other tissue. Sufficient pressure may be applied to rupture a synovial cyst or to increase the fluid communication between the facet joint and a synovial cyst. The medical procedure may include injecting a fluid composition into the facet joint or directly into a synovial cyst wherein the fluid composition comprises at least one component to liquefy or decompose tissue within the synovial cyst. Such a component may be an active component such as a hyaluronidase or a collagenase. After injecting a fluid composition, a medical procedure may include removing liquid from the facet joint, for example to also draw fluid from a synovial cyst, or to remove liquid directly from a synovial cyst, for example by inserting a fluid suction tool through the sheath and through the facet joint to directly penetrate into the volume of an anterior synovial cyst. Removing liquid from the facet joint or directly from a synovial cyst may be performed after a wait time to permit the hyaluronidase or collagenase to reduce the viscosity of tissue within the synovial cyst to facilitate enhanced aspiration. Such a wait time may be on the order of minutes or hours. In some implementations, such a wait time may be at least 5 minutes, at least 20 minutes or at least 30 minutes. In some implementations such a wait time may be less than 4 hours, less than 3 hours, less than 2 hours or less than 1 hour. In some implementations, the wait time may be for a more extended time, for example overnight or even a few days, with aspiration to remove liquefied synovial cyst material occurring on a later day than the day on which the fluid composition containing the active agent is provided to a synovial cyst. A medical procedure may include irrigating through the facet joint or directly irrigating a synovial cyst, which may assist in removing liquefied material from the synovial cyst. The medical procedure may include a tissue ablation procedure, for example RF ablation, cryoablation or ultrasound ablation. Such a tissue ablation procedure may be performed by transmitting an ablation tool through the sheath and through the facet joint to directly access the volume of a synovial cyst.

Following one or more such medical procedures, a tissue ablation procedure may be performed to ablate at least a portion of the synovium at the posterior side of the facet joint. Such tissue ablation may include RF ablation, cryoablation, ultrasound ablation or chemical ablation. In some implementations, such tissue ablation may be performed by RF ablation using one or more components of a facet joint surgical tool of the facet joint surgical tool aspect to transmit the RF energy to a distal area of the facet joint surgical tool, as described elsewhere in this disclosure. Such a tissue ablation procedure may form an artificial cavity in or adjacent to the posterior side of the facet joint to provide a volume to receive synovial fluid as an alternative to pressurizing an anterior side of the facet joint, which may result in recurrence of an anterior synovial cyst. Such an artificial cavity may provide an open volume to relieve pressure from the anterior side of the facet joint. The method may include a first tissue ablation procedure at the posterior side of a facet joint to prepare such an artificial cavity. After such first tissue ablation procedure, the method may include a second tissue ablation procedure to the posterior side of the facet joint at a location posterior of the location of the first tissue ablation procedure. The second tissue ablation procedure may be directed to destroying at least a portion of the synovium on the posterior side prior to termination of the surgical procedure.

The method may include use of a facet joint surgical tool of the facet joint surgical tool aspect to perform some portion of the method. The method may include, prior to the retracting the facet joint, penetrating into tissue of a patient with a distal piercing tip of a facet joint surgical tool, such as of the facet joint surgical tool aspect. After such penetrating, a piercing tip of a facet joint surgical tool may be advanced through tissue of the patient to the posterior side of the facet joint and the facet joint may be retracted by rotating rotatable members of the facet joint surgical tool to reposition distal tips of the rotatable members from a facet joint penetration configuration to a facet joint retraction configuration. Stylets may be disposed through lumens through the rotatable members during the penetrating. Such stylets may be removed before or after reconfiguring the facet joint surgical tool for retraction of the facet joint. The method may include, after retracting the facet joint with distal tips of the rotatable members, advancing the sheath of a facet joint surgical tool into the facet joint to a depth to effect retraction of the facet joint with the sheath, permitting the rotatable members to be used for performing a medical procedure or permitting such rotatable members to be removed from the sheath to provide an access route for inserting other tools to the vicinity of the facet joint for use in a medical procedure. A variety of insertable tools may be advanced through the sheath into the patient for use and performing a medical procedure. Such insertable surgical tools may include fluid injection and/or aspiration tools, wires or flexible needles for accessing and puncturing the anterior synovial cyst, and ablation tools. Alternatively, one or more such insertable tools, for example catheter-type tools, may be inserted through a lumen of rotatable member while the rotatable member is still disposed through the sheath.

The method may include penetrating into a facet joint capsule of a facet joint using the facet joint surgical tool with rotating members positioned in a facet joint penetration configuration. The penetrating may comprise advancing at least distal tips of the rotating members into the facet joint capsule. After penetrating into the facet joint capsule, the method may include rotating the rotatable members to reconfigure the rotating members to a facet joint retraction configuration. With the rotatable members in such a facet joint retraction configuration, the facet joint may be retracted, or widened, in a manner to permit a variety of medical procedures to be performed in the vicinity of the facet joint, for example in or through the facet joint, for example one or more medical procedures as described above. After reconfiguring the rotatable members to the facet joint retraction configuration, the sheath may be advanced from outside to inside of the facet joint capsule, and the sheath may maintain the facet joint in a retracted position. After the penetration into the facet joint capsule, a fluid composition may be conducted through a lumen of at least one of the rotating members to exit the lumen in the vicinity of the facet joint. Fluid may also be aspirated from the vicinity of the facet joint through the lumen of the other rotating member, such as may be appropriate for an irrigation procedure. A medical device may be conducted through the lumen of one of the rotating members to the vicinity of the facet joint, and a medical operation may be performed in the vicinity of the facet joint using the medical device. Such a medical device may be a surgical device. At least one of the distal portions of the rotating members may be a RF electrode and the method may include operating the RF electrode to perform a RF ablation procedure on tissue in the vicinity of the facet joint.

In another aspect of the disclosure, a method may include treating a facet joint synovial cyst, whether located on a posterior side of the facet joint or an anterior side of the facet joint, with a method including introducing into tissue of the synovial cyst a fluid composition including at least one active component, or active agent, to decompose or liquefy tissue within the synovial cyst. When treating a facet joint synovial cyst located on an anterior side of the facet joint, access to the synovial cyst may be as described with respect to the method aspect above for treating a synovial cyst on an anterior side of a facet joint. When treating a synovial cyst located on a posterior side of the facet joint, the synovial cyst may be directly accessed from the posterior side of the patient using minimally invasive surgical tools to penetrate tissue and advance to a depth of the synovial cyst. Such treatment of a posterior synovial cyst may be performed using the facet joint surgical tool of the facet joint surgical tool aspect, even though access to the synovial cyst does not require providing access through the facet joint. The posterior synovial cyst may be pierced directly with a piercing tip of the facet joint surgical tool. Needle tips of the rotatable members may be rotated to cut tissue within the synovial cyst. The fluid composition may be introduced directly into the synovial cyst from lumens through the rotatable member. Tissue of the synovial cyst may be ablated using an insertable ablation tool inserted through a lumen of a rotatable member or through the sheath with the rotatable members removed. Alternatively, tissue ablation may be performed using one or more components of the facet joint surgical tool to transmit the RF energy to the tissue to be ablated. The method may include, after treating the synovial cyst, performing one or more tissue ablations, for example to destroy at least a portion of the synovium on the posterior side of the facet joint, as described elsewhere.

Further aspects of the disclosure include the use of a hyaluronidase or other collagenase for treatment of a facet joint synovial cyst, which may be located posterior of a facet joint or anterior of a facet joint.

These and other aspects of the disclosure, and other additional features and feature refinements applicable to these and other aspects of the disclosure, will be apparent with reference to the following Detailed Description, the drawings and the claims.

BRIEF DESCRIPTION OF THE DRAWINGS

FIGS. 12-15 illustrate a kit and components thereof.

FIG. 29 illustrates use of a rotatable member of a facet joint surgical tool as a RF electrode for performance of a RF tissue ablation procedure.

DETAILED DESCRIPTION

Figure 1:
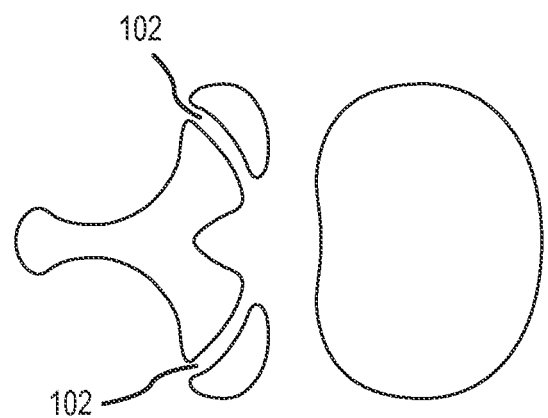
FIG. 1 illustrates generally facet joints.

For a more complete understanding of the invention and aspects thereof, reference is now made to the following Detailed Description taken in conjunction with the figures.

In one embodiment, an access device is formed by two elongated round hollow metal tubes of circular cross-section. The ends of the tubes may be cut at an angle. The tube edges may be sharpened, such as a pointed tip of a spinal needle or hypodermic needle. The two tubes may be inserted through and constrained by a smooth outer sheath. Thus the outer sheath may be oval shaped in cross section and rigid. The rigid sheath may prevent the tubes from crossing or overlapping during insertion or rotation of the tubes. The sheath may be sized to allow the tubes to freely rotate. Before the access device is inserted into the skin and deep tissues, the angled ends of the tubes may first be rotated to face in opposite directions. The two sharpened edges may now form a single blade-like surface. For convenience such a device may be referred to as a rotatable blade access device ("Rbad" for short). The sharpened tip of the Rbad acting like a single needle allows the two tubes to pierce the skin and tissues and be placed smoothly into the desired location. The tip of the Rbad is placed in the facet joint. In one method the device Rbad is placed with the blade edges parallel to the facet joint surface. After the Rbad tip is placed in the facet joint then the two tubes are each rotated 180 degrees. The blade tips are now separated forcing the two articular surfaces of the facet joint apart creating a retracted working space for instruments or medications and also forming a slit in the joint capsule. The maximum distance the tips of the tubes may be separated, and therefore the two surfaces of the facet joints separated, is equal to the sum of the outer diameters of the tubes. If desired the tubes may be rotated separately or in increments. Therefore the facet joint may be widened gradually ranging from the minimal width of the thin tip of the Rbad before rotation to the maximal width equal to the sum of the outer diameters of the two tubes. In one embodiment the outer sheath is made of metal and is rigid and formed from a material such as stainless steel. The metal oval sheath may then be wedged into the joint, and the sheath may then serve as a portal allowing for passage of other larger instruments into the joint during treatment. After a cyst is treated the sheath may then be rotated 90 degrees, so that the long axis of the oval shaped cross section of the sheath is now parallel to the joint surfaces to allow for easy removal of the sheath from the facet joint.

In one embodiment of a method, the blade-like dual lumen tip of the Rbad is placed perpendicular to the facet surface. The blades may then be rotated and thus opened to incise a slit in the facet capsule parallel to the surfaces of the facet joint. Then the oval outer sheath may be pushed, wedged or hammered into the joint. Then the oval shaped sheath may be rotated 90 degrees to widen the facet joint opening.

In some patients joints may be severely arthritic. Bony osteophytes or spurs may bridge and therefore obstruct access to the joint. In these patients the same oval access sheath trocar may be used. The Rbad is placed against the back of the facets and then the rotatable tubes are rotated rapidly to drill and remove the bone over the back of the facet. Alternatively, instead of using the Rbad two drill bits of similar diameter to the tubes may be used to remove the bone covering the back of the narrow joints. Then in either case the Rbad may be positioned to retract the joint or the oval access sheath may be wedged and rotated to widen the joint.

All these methods and devices allow access to the now widened facet joint. Then if desired, another instrument such as, for example a radiofrequency ablation electrode, coaxial trocar or endoscopy, may be passed either into the retracted open joint or navigated into or near to the facet capsule or synovial cyst.

If RF ablation is used in another embodiment, the outer sheath may be made of plastic or other electrically insulating material. Alternatively the Rbad, except for a distal portion, may covered with an insulating material and the tip may then be used as a RF ablation device.

In another embodiment of a method, the joint is accessed with the Rbad and the joint directly aspirated. Synovial cysts communicate with the adjacent joint and therefore the synovial cyst may be aspirated indirectly when the joint is aspirated. If the fluid is too thick to aspirate, then a hyaluronidase may be injected. The dual tube design allows for easy injection of hyaluronidase or other treatment composition into the joint. The retractor opens the joint and widens the communication between the cyst and joint and allows the medication (e.g., hyaluronidase) to more easily flow into the cyst. Hyaluronidases are enzymes that are used for digesting proteins. This has been used clinically to reduce scar formation in the cornea and also to remove excess collagen from cosmetic procedures. Also collagenases have been used clinically to reduce and dissolve scar tissue in peronie's disease and dupuytren's contracture. A collagenase safely digests the collagen in scar tissue Hyaluronidase safely digests proteins liquifying the viscid synovial fluid in the joint and cyst. This facilitates aspirating the very thick, gel-like synovial fluid within the cyst through the small tubes of an Rbad or, if desired, through the outer oval sheath.

The wall of a synovial cyst is typically thinner and weaker than the capsule of the adjacent joint. In another embodiment of a method a fluid, such as for example saline, is injected through the Rbad to distend and pressurize the capsule and communicating cyst until there is a sudden loss of resistance in the system indicating cyst rupture. The pressure on the spinal canal is then relieved. Myelogram contrast media may be injected into the joint to visualize the cyst and joint capsule. A successful endpoint of such a treatment may be visualization of contrast in the epidural space of the spinal canal. This procedure may be referred to as a trans-facet epidurography. The trans-facet epidurogram can be imaged with either CT, fluoroscopy or MRI. In another embodiment, after the cyst is ruptured a hyaluronidase and/or a collagenase is injected through the facet into the epidural space to reduce adhesions, scarring and recurrence of the cyst.

It is observed that anterior cysts are rarely seen associated with posterior located cysts. The anterior cysts are usually symptomatic because the nerves and sensitive tissues are located in front of the joint. A further use of the device is to create an artificial cyst along the back of the joint to reduce the pressure in the anterior joint and help prevent recurrence. In one embodiment of a method, after treatment the Rbad is positioned on the back of the facet capsule and the blades are rotated either in the same direction or in opposite directions rapidly creating a cavity. Fluid is injected through one lumen and aspirated by vacuum through the other lumen. In another embodiment of a method the Rbad is positioned just within or posterior to the joint and a radiofrequency lesion is performed ablating the posterior capsule and synovium and creating an artificial cyst-like cavity. One or more lesions may be created. The artificial cysts act as reservoirs thus decreasing the pressure in the joint and anterior capsule reducing the risk of recurrence of the symptomatic anterior cyst. If desired, surgery, focused ultrasound, coblation techniques or laser energy may be used to create such an artificial posterior cyst cavity.

In a further embodiment, the Rbad dual tubes may function as either a unipolar or bipolar RF electrode, and the tubes may be either slowly or rapidly rotated. This may provide an improvement relative to stationary RF electrodes as rotating electrodes distribute the RF energy more uniformly. Also certain trajectories of motion distribute energy more uniformly and efficiently than others.

In another embodiment of a method, the cyst is directly accessed and treated with the Rbad with a or coaxial tube or insulated wire inserted through a tube or sheath of the Rbad.

In another embodiment of a method, the neck of a cyst may be accessed by a Rbad or coaxial tube or insulated wire inserted through a tube of sheath of the Rbad. The cyst is first aspirated and/or ruptured and then the neck of the cyst is ablated preventing recurrence. The neck of the cyst may be treated for example with RF ablation or cryoablation to occlude the channel between the cyst and joint.

The synovium of the joint produces the fluid filling the joint and distending the cyst. In one preferred embodiment, the cyst wall and facet capsule may be ablated with RF energy. This embodiment is specifically directed at synovial ablation. Conductive fluid such as saline may be circulated through the system increasing the effective size of the Rbad electrode allowing for ablation of more synovium. This partially ablates the synovium, reducing the production of synovial fluid and reducing the risk of recurrence of the cyst. This also treats pain by reducing capsular distension and treating posterior capsular structures. In variations of this embodiment the Rbad may be used either as the primary method of percutaneous treatment or prior to, after or during an open surgical procedure to reduce the risk of recurrent synovial cysts of the facet joints after surgery.

Since there are two tubes, which may be in the form of needles (e.g., spinal needles or hypodermic needles), forming the tip of the Rbad device, fluid may be circulated in the system by injecting or pumping fluid through one tube and aspirating fluid by suction or vacuum through the other tube. This allows the operator to remove debris, small bone or cartilage fragments and blood by circulating fluid thus flushing and cleaning both the joint and cyst.

The Rbad is a multipurpose device that may function as a tissue resector, trocar, drill, access device, retractor, irrigator and/or RF ablation electrode.

Figure 2:
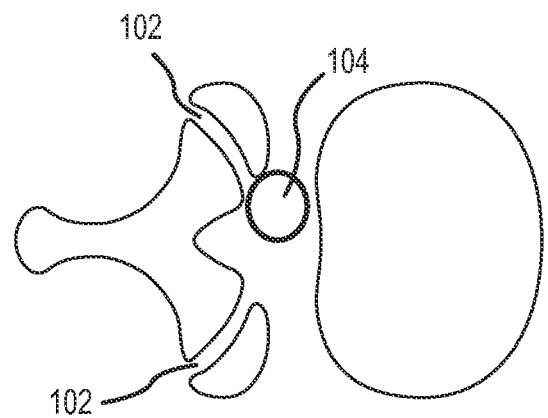
FIG. 2 illustrates a facet joint with a synovial cyst located anterior to the facet joint.
Figure 3:
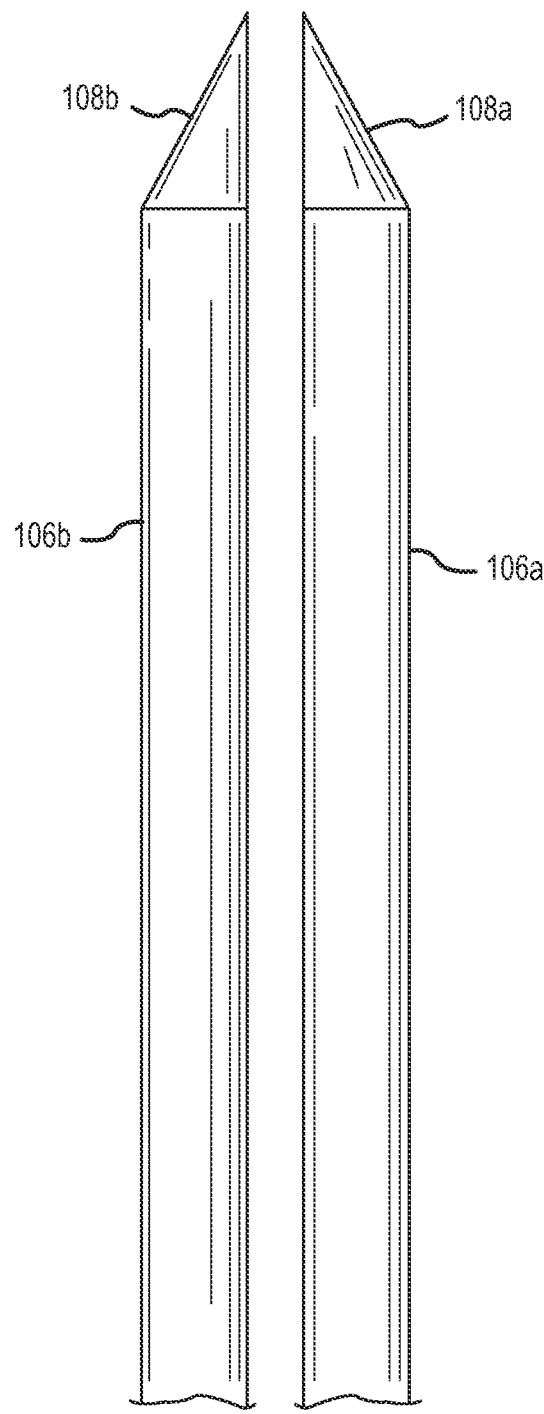
FIG. 3 illustrates rotatable members useful for a facet joint surgical tool.
Figure 4:
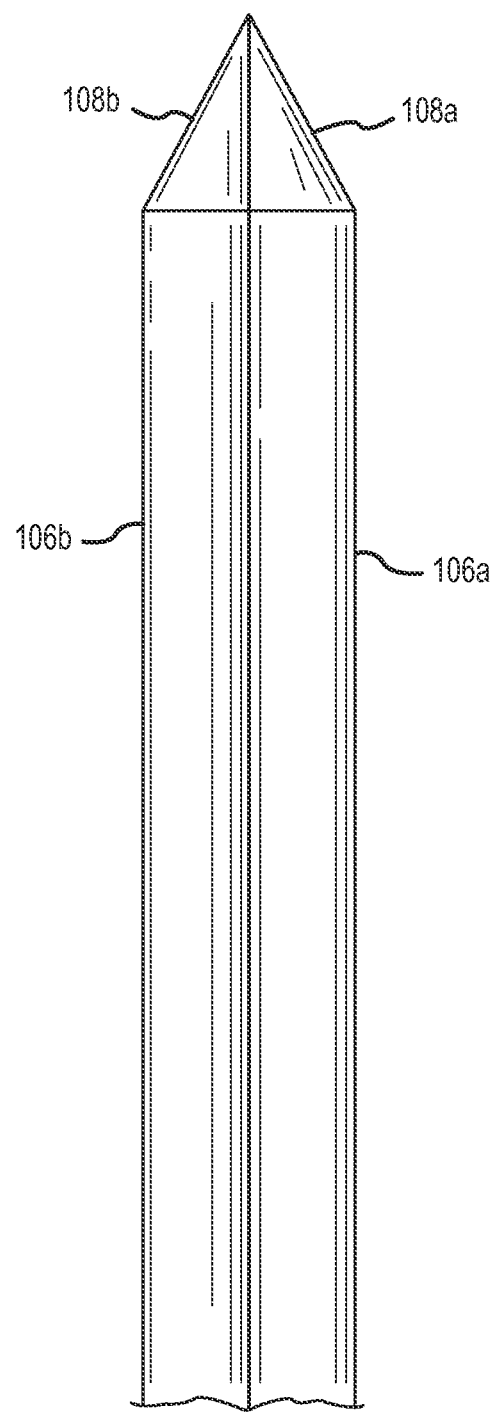
FIG. 4 illustrates the rotatable members of FIG. 3 oriented in a facet joint penetration configuration with a piercing tip.
Figure 5:
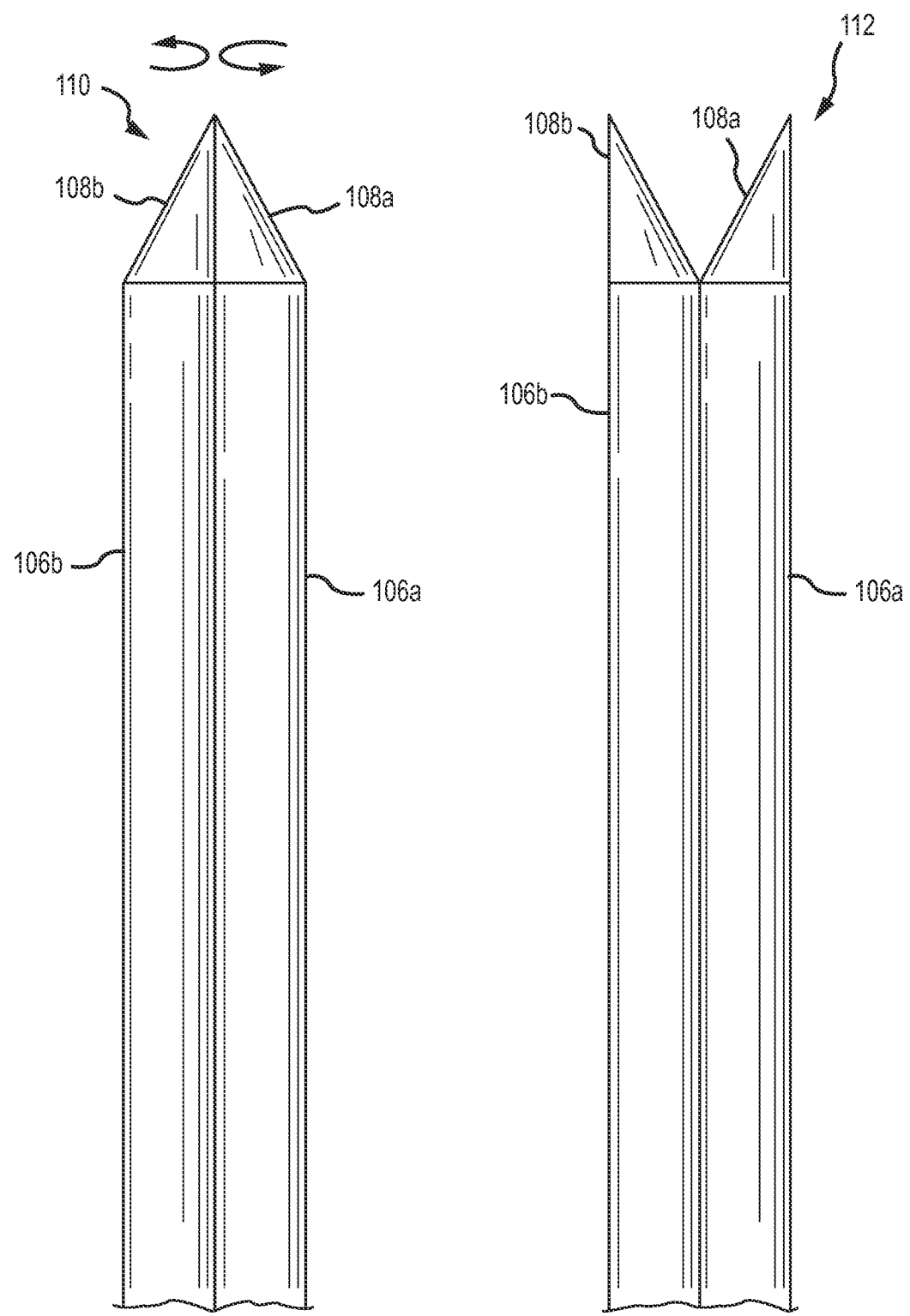
FIG. 5 illustrates the rotatable members of FIG. 4 being reconfigured from a facet joint penetration configuration to a facet joint retraction configuration.

FIG. 1 illustrates a portion of a vertebral column showing the general location of facet joints 102 between superior and inferior processes of the vertebrae. FIG. 2 is an illustration of a portion of a vertebral column as shown in FIG. 1, but showing a synovial cyst 104 located anterior to a facet joint 102. FIG. 3 is an illustration of two rotatable hollow members 106 (e.g., tubes, needles) with pointed distal portions 108 that may be used as rotatable members, or tubes, of an Rbad. FIG. 4 shows the same two hollow members 106 as shown in FIG. 3 in adjacent relation as they may be constrained within a sheath of a Rbad and with the hollow members 106 rotated to relative positions where the distal portions 108 are in a facet joint penetration configuration with distal portions positioned to form a piercing tip to pierce through tissue and penetrate into a facet joint. In a preferred facet joint penetration configuration the hollow members are adjoining, with no or essentially no gap between them as constrained within a sheath. FIG. 5 is an illustration of the same hollow members 106 as shown in FIGS. 3 and 4 and showing rotation of the hollow members 106 about their respective longitudinal axes to change the positioning of the distal portions 108 between a facet joint penetration configuration 110 and a facet joint retraction configuration 112. Arrows in FIG. 5 show an example of relative rotation of the hollow members 106 to change from the facet joint penetration configuration 110 to the facet joint retraction configuration 112.

Figure 6:
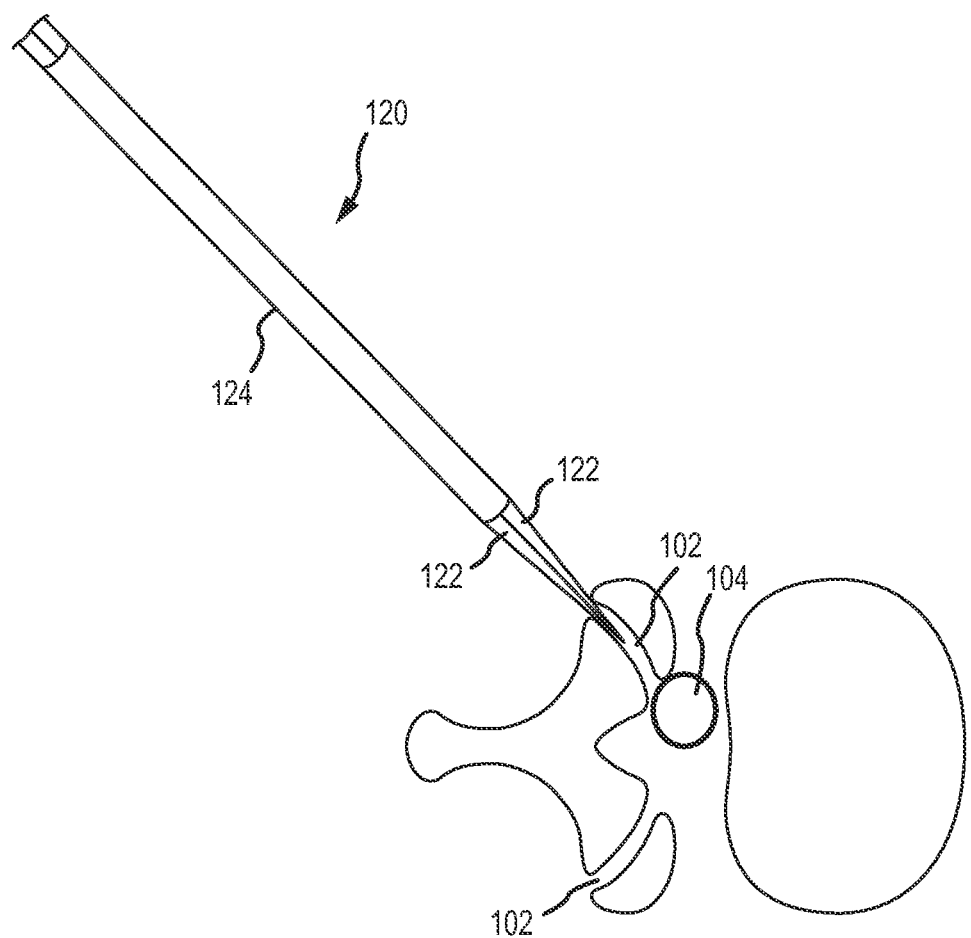
FIG. 6 illustrates a facet joint surgical tool with rotatable members disposed through a sheath and configured with a piercing tip penetrating into a facet joint from a posterior side.
Figure 7:
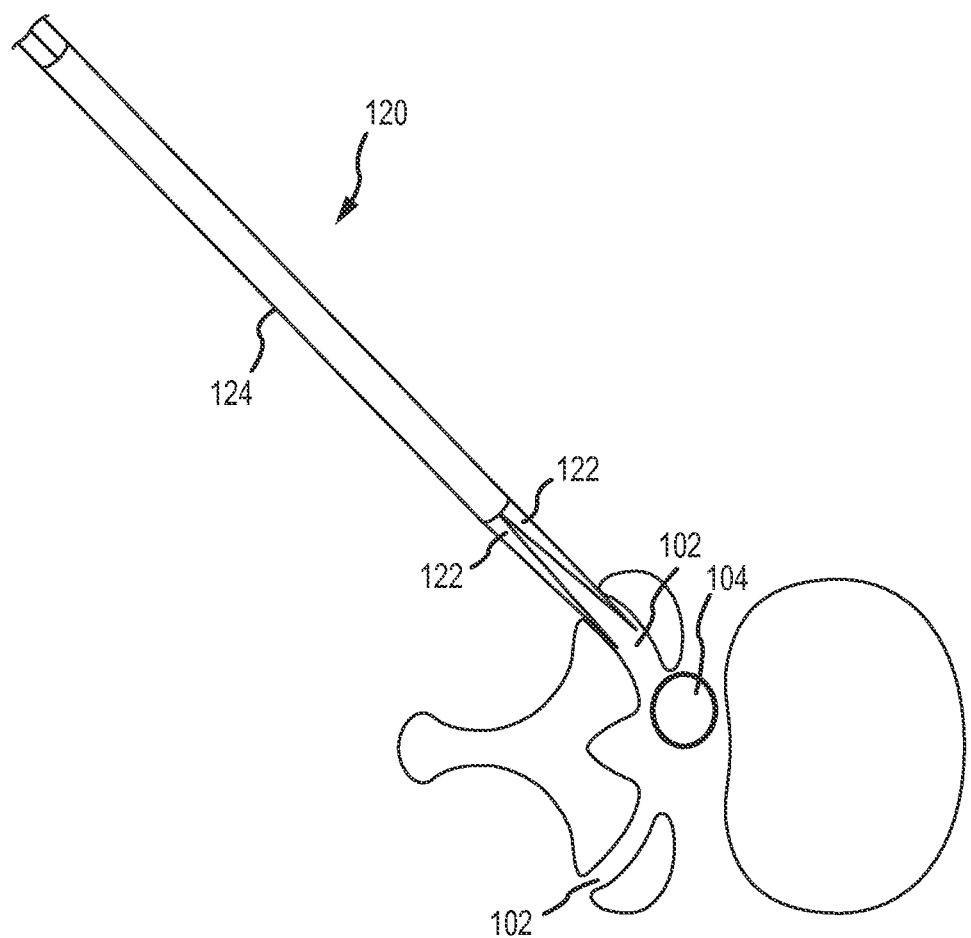
FIG. 7 illustrates the facet joint surgical tool of FIG. 6 with rotatable members reconfigured to retract a facet joint.
Figure 8:
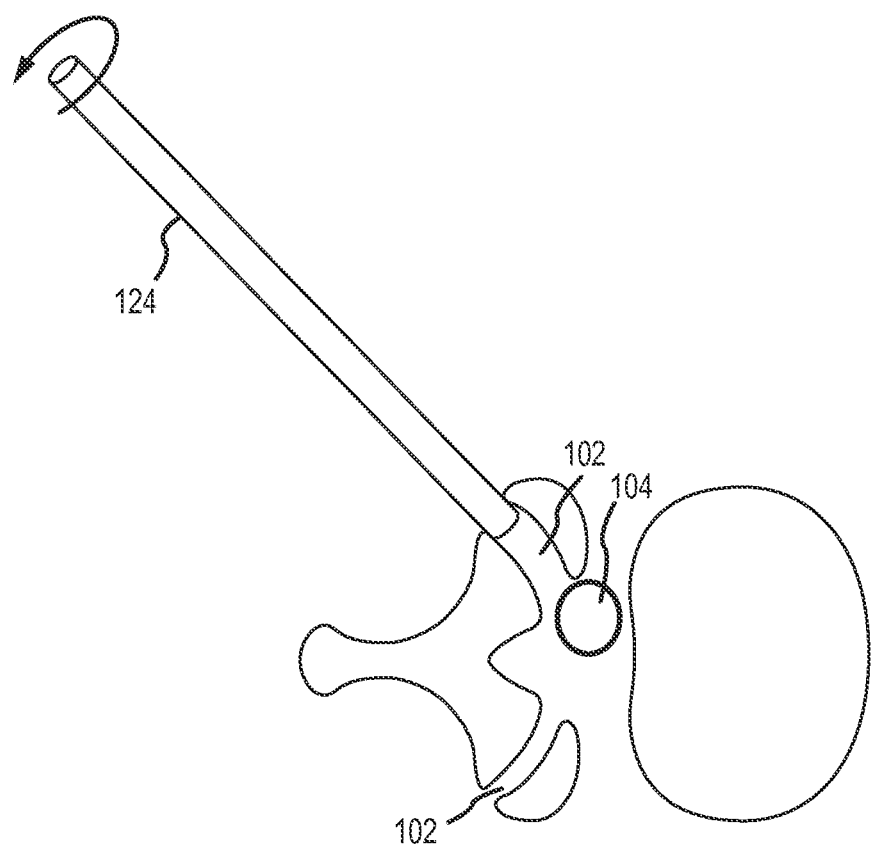
FIG. 8 illustrates the sheath of the facet joint surgical tool of FIGS. 6 and 7 after advancement of the sheath to retract the facet joint and removal of the rotatable members from the sheath.
Figure 9:
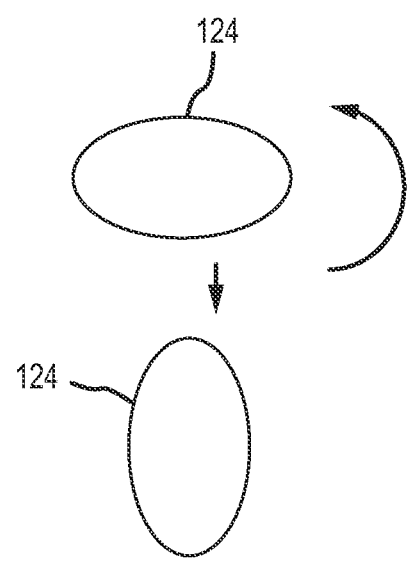
FIG. 9 illustrates rotation of the sheath of FIG. 8 to adjust retraction of a facet joint with the sheath.
Figure 10:
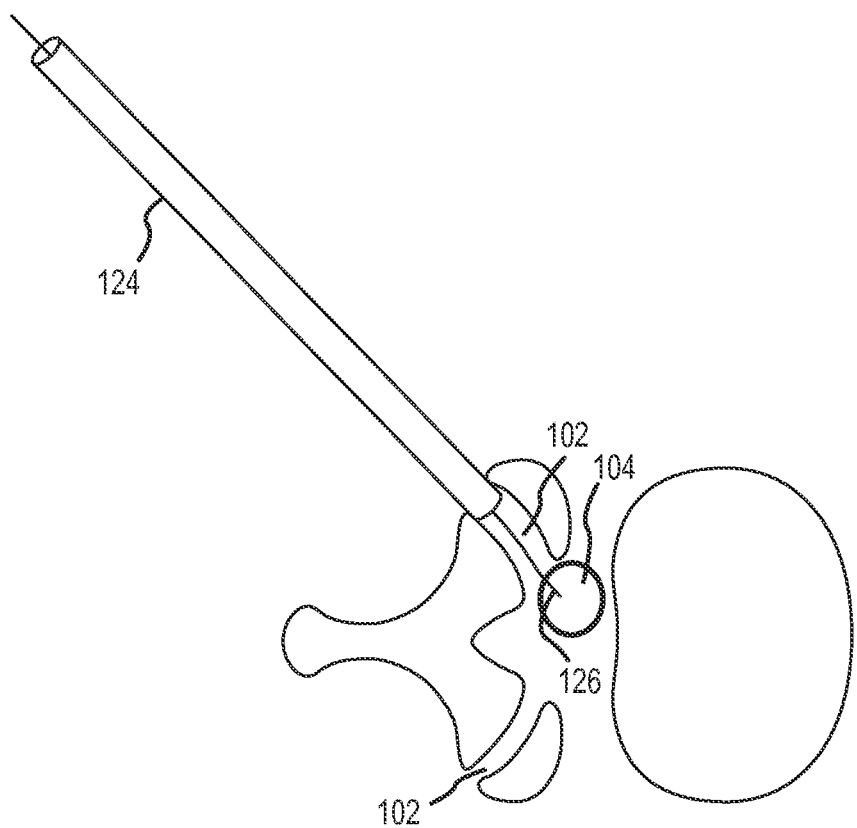
FIG. 10 illustrates passage of a surgical tool through the sheath of the facet joint surgical tool of FIGS. 6 and 7 with the rotatable members removed.

FIG. 6 is an illustration showing a facet joint surgical tool 120 (e.g., a Rbad) with two rotatable hollow members 122 disposed through a sheath 124 and positioned in a facet joint penetration configuration with a tissue piercing tip that has penetrated into the facet joint 102. FIG. 7 shows the same surgical tool 120 with the hollow members 122 rotated to position the pointed distal portions of the hollow members in a facet joint retraction configuration to widen the facet joint 102 following penetration into the facet joint 102. FIG. 8 shows the sheath 124 of the same surgical tool 120 after the sheath 124 has been advanced into the facet joint to maintain retraction of the facet joint. As shown in FIG. 8, the hollow members 122 have been removed from the sheath 124, permitting the sheath 124 to be used as a conduit for conduction other medical tools or fluid compositions into or through the retracted facet joint 102. The arrow in FIG. 8 shows that the sheath 124, which has an oval cross section, may be rotated between retracting and non-retracting positions, which are illustrated in FIG. 9. In a retracting position, the major, or long, axis of the oval cross-section of the sheath 124 is perpendicular to the facets of the facet joint, and the ends of the sheath 124 at opposite ends of the long axis of the oval cross-section push against the facets and wedge the facet joint into a retracted, or widened position. In a non-retracting position, the minor, or short, axis of the oval-cross section of the sheath 124 is perpendicular to the facets and the facet joint 102 is in an unretracted or less retracted situation. The non-retracting position of the sheath may be beneficial, for example, to permit easier withdrawal of the sheath 124 from the facet joint 102, for example at the conclusion of a surgical procedure. FIG. 10 shows the sheath 124 used as a conduit to conduct a medical tool 126 (e.g., a wire) to the facet joint 102 and through the facet joint 102 to the vicinity of the cyst 104, for example to perform a surgical operation on or in the vicinity of the cyst 104 (e.g., to puncture the cyst).

Figure 11:
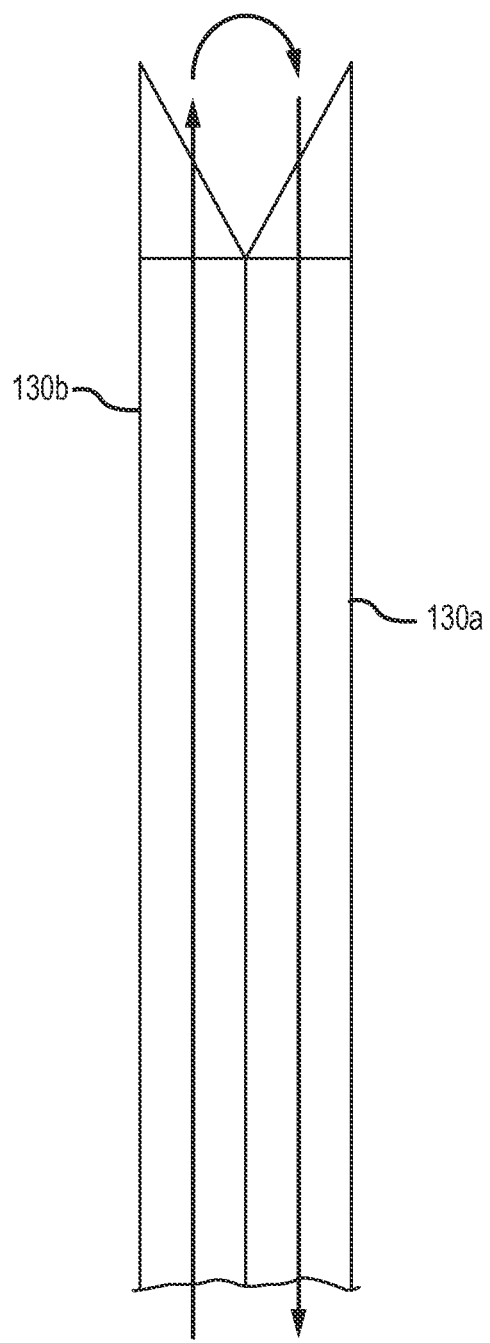
FIG. 11 illustrates circulation of liquid, such as irrigation liquid, using lumens of rotatable members.

FIG. 11 shows adjacent rotatable hollow members 130 with pointed distal end portions positioned in a facet joint retraction configuration, and with arrows showing a possible fluid circulation path with fluid being delivered from one hollow member 130*b* and aspirated through the other hollow member 130*a*. Such fluid circulation may, for example, be used to irrigate in the vicinity of a facet joint.

Figure 12:
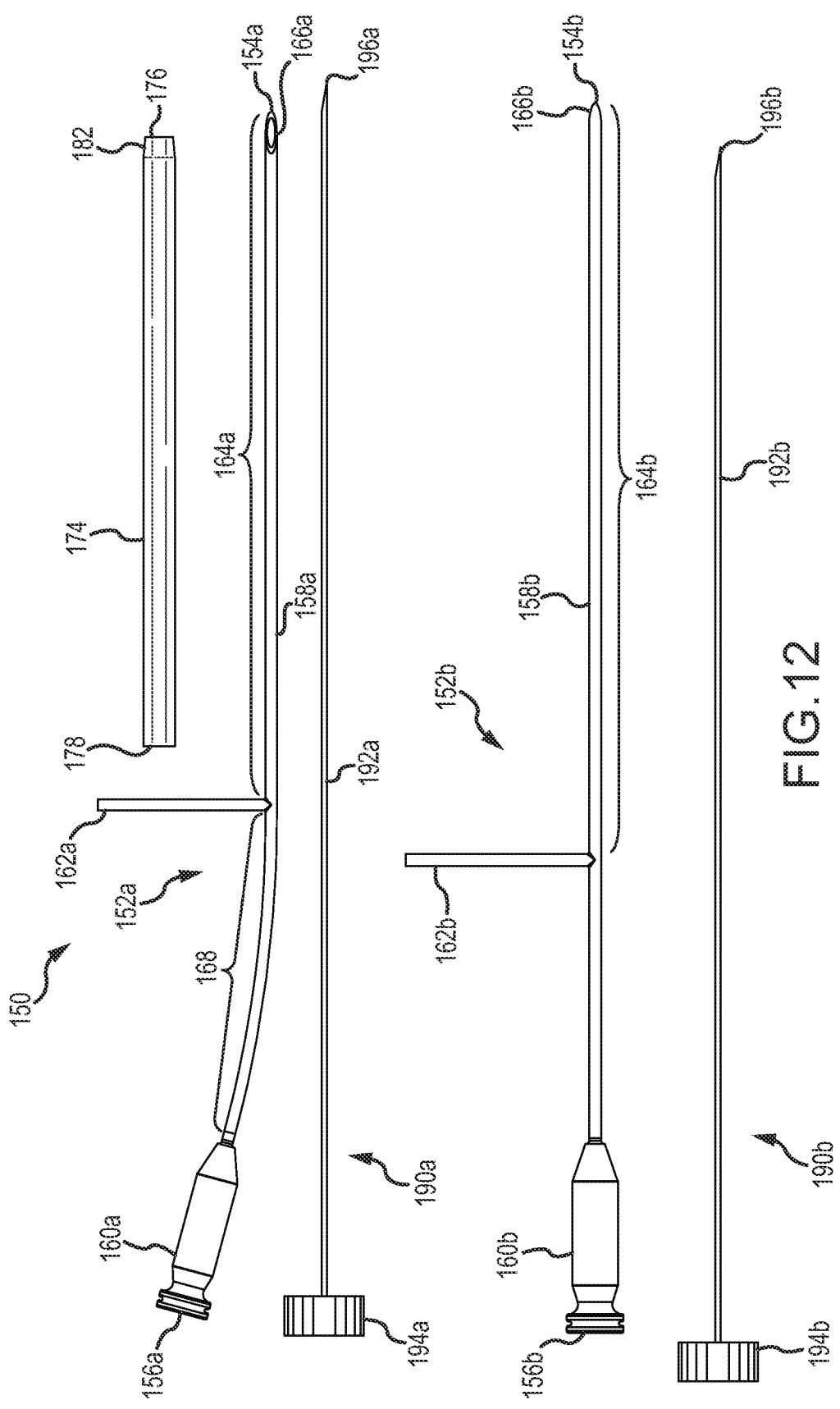

Reference is now made FIGS. 12-17 illustrating one example embodiment of a kit with components useful for performance of a medical procedure in the vicinity of a facet joint, for example to treat a synovial cyst. Shown in FIG. 12 is an example kit 150 with components assemblable into facet joint surgical tool configurations. The kit 150 include first and second rotatable working pieces 152*a,b*, each having a distal end 154*a,b* and a proximal end 156*a,b* and with a rotatable member 158*a,b*, fluid connection hub 160*a,b* and rotation actuation handle 162*a,b*. The rotatable members 158*a,b* include insertion portions 164*a,b* disposed distal of the corresponding rotation actuation handle 162*a,b* and non-insertion proximal portions including connection locations for the rotation actuation handles. As shown in FIGS. 13C and 14C, the rotatable members 158*a,b* include distal portions 166*a,b* that taper toward the distal tips 154*a,b*. The rotatable member 158*a* of the working piece 152*a* includes an arcuate portion 168 with a bend that helps to keep the fluid connection hubs 160*a* and 160*b* from interfering when the rotatable members 158*a* and 158*b* are rotated relative to one another. The bend of the arcuate portion 148 also makes it easier to connect the fluid hubs 160*a*, 160*b* with fluid manipulation devices (e.g., syringes) without the fluid manipulation devices interfering with each other.

Figure 15A:
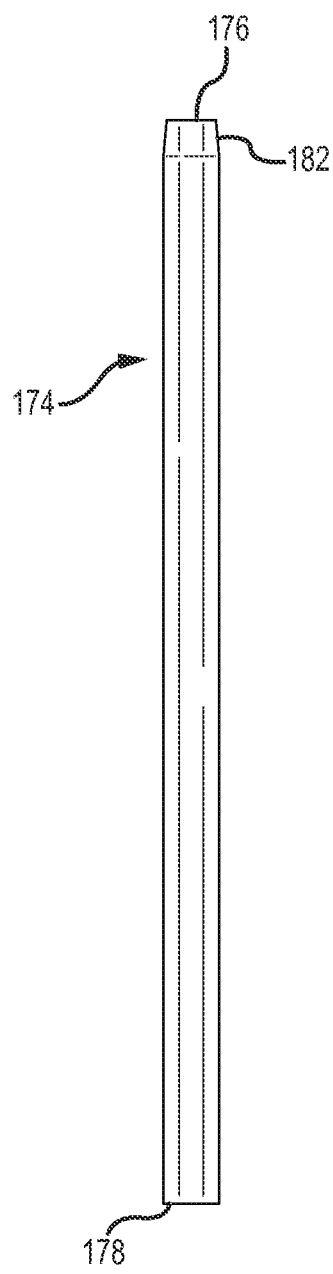
Figure 15B:
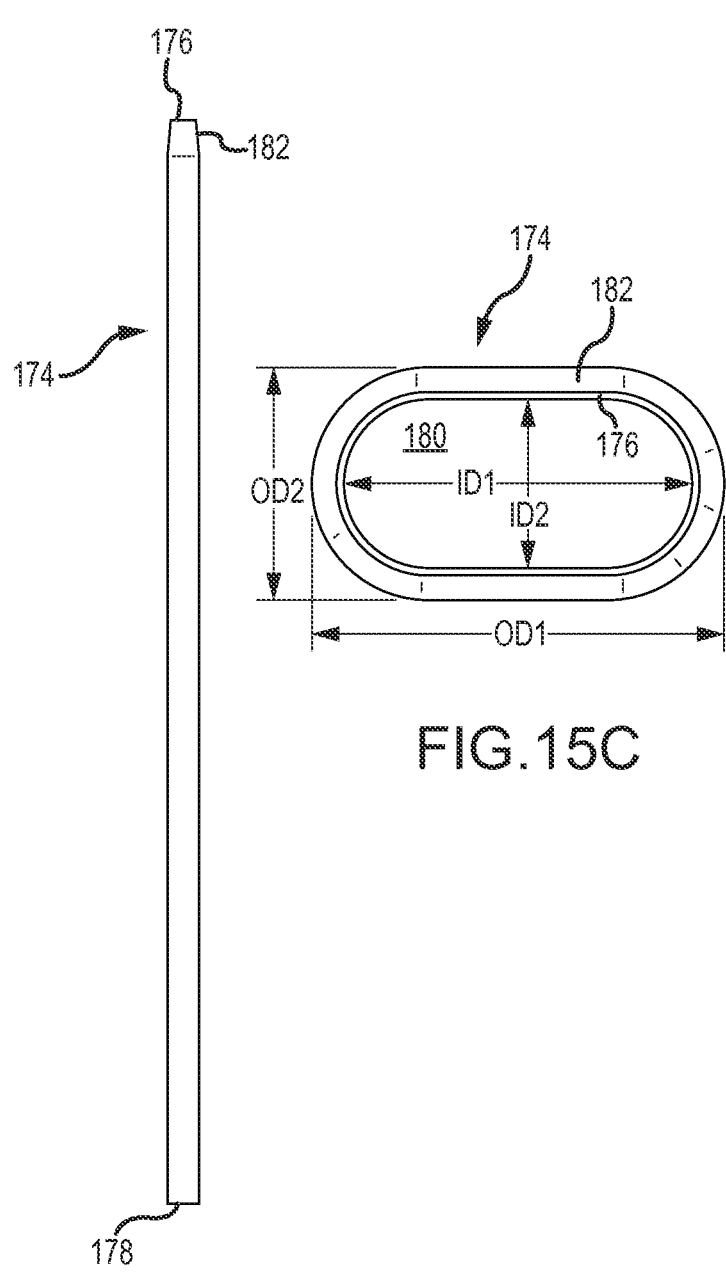

The kit 150 includes a sheath 174 including a distal end 176 and a proximal end 178. The sheath 174 includes an internal passage therethrough sized to receive and constrain in a side-by-side relationship the insertion portions 164*a* and 164*b* of the rotatable members 158*a,b*. The sheath 174 includes a tapered distal end portion 182 adjacent the distal end 176 of the sheath 174. In the tapered distal end portion 182, the exterior cross-section of the sheath 174 reduces in size toward the distal end 176 as the thickness of the sheath wall is reduced toward the distal end 176 along the tapered distal end portion 182. The cross-section of the internal passage 180 is constant through the entire length of the sheath 174. The sheath 174 includes a maximum exterior cross-section, as best shown in FIG. 15C, that includes a larger first cross dimension OD1 than the second cross dimension OD2. So that the maximum exterior cross-section of the sheath 174, and therefore also the insertion cross-section of the sheath 174, has an aspect ratio (OD1/OD2) of larger than one. Likewise, the minimum area cross-section within the internal passage 180 includes a first cross dimension ID1 that is larger than the second cross dimension ID2 and therefore also has an aspect ratio (ID1/ID2) of greater than one.

The kit 150 also includes two stylets 190*a,b* including solid needle insert members 192*a,b* extending from hand-manipulable heads 194*a,b*. The stylets 190*a,b* include pointed distal tips 196*a,b*. The stylets 190*a,b* are configured for insertion of the needle insert members 192*a,b* through the working pieces 152*a,b* with the distal tips 196*a,b* corresponding with the distal ends of lumens through the rotatable members 158*a,b* adjacent the distal tips 154*a,b*, to block the distal ends of the lumens to prevent tissue coring when the rotatable members 158*a,b* are positioned in a piercing configuration and used to pierce through tissue during a surgical procedure. The fluid connection hubs 160*a,b* and the heads 194*a,b* of the stylets 190*a,b* may have corresponding keyed features that properly align beveled stylet ends at the distal tips 196*a,b* with beveled needle points of the distal end portions 166*a,b* or the rotatable members 158*a,b* when the insertion needle members 192*a,b* are fully inserted through the rotatable working pieces 152*a,b* with the heads 194*a,b* engaged with the fluid connection hubs 160*a,b*.

Figure 16:
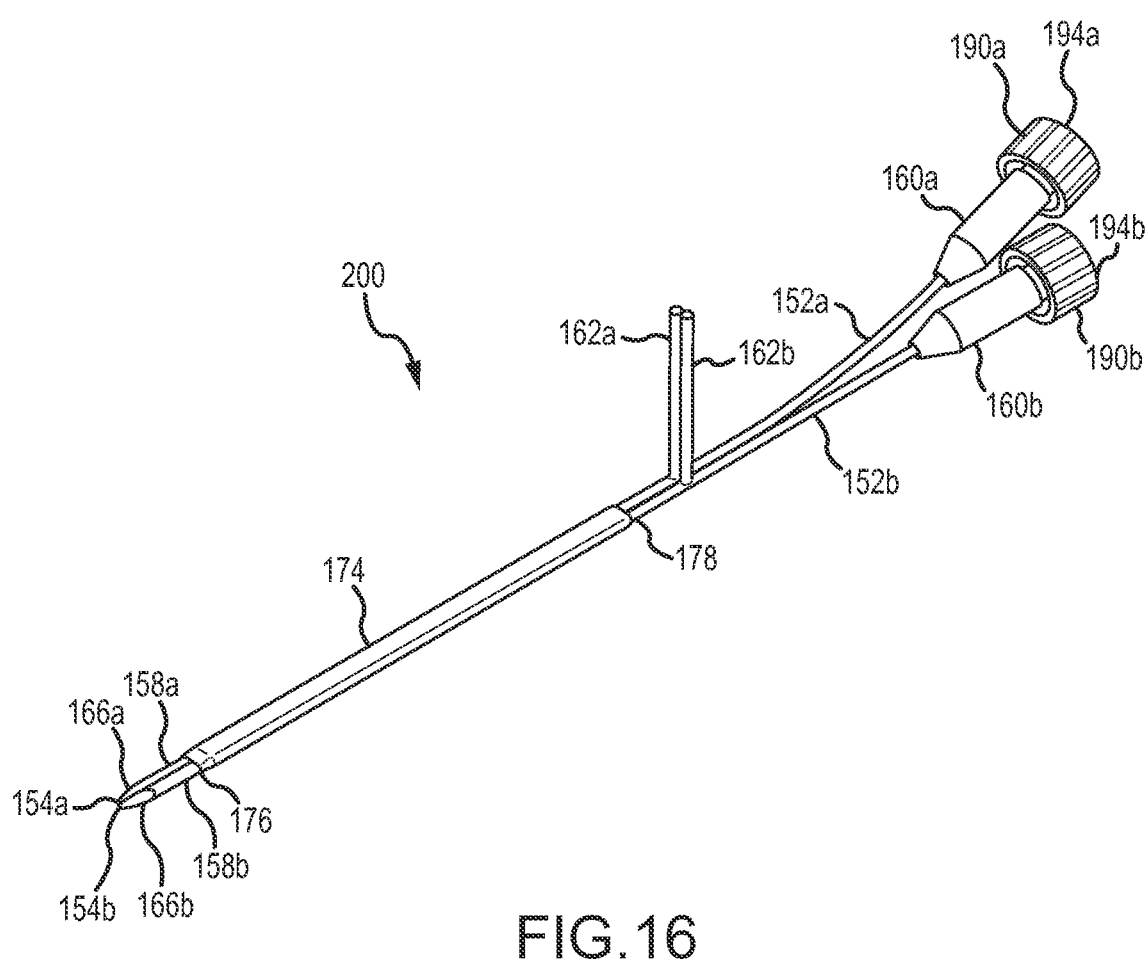
FIGS. 16 and 17 illustrate an assembled facet joint surgical tool using components of the kit of FIGS. 12-15 with rotatable members configured in a facet joint penetration configuration and facet joint retraction configuration, respectively.
Figure 17:
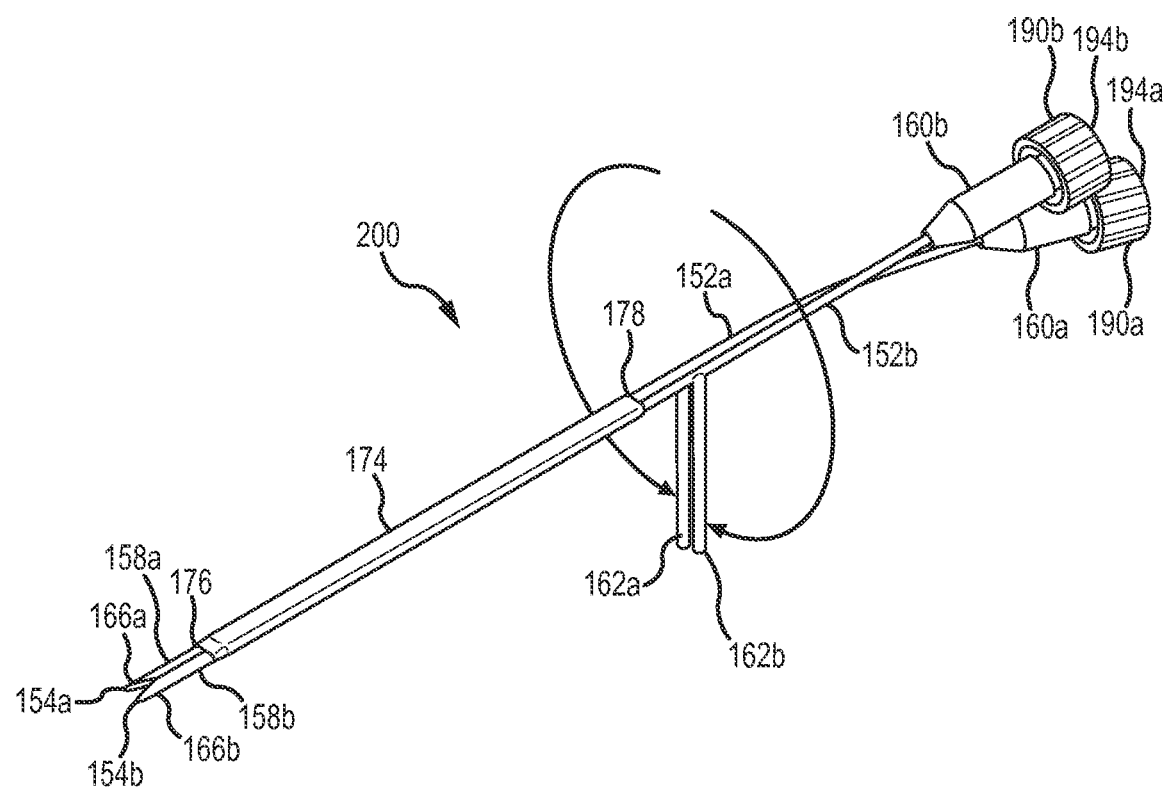

FIGS. 16 and 17 illustrate an example facet joint surgical tool 200 including an assembly of the working pieces 152*a,b*, sheath 174 and stylets 190*a,b* of the kit 150. In the assembly of the facet joint surgical tool 200, the insertion portions of the rotatable members 158*a,b* are disposed through the internal passage of the sheath 174 with the distal tips 154*a,b* disposed distal of the distal end 176 of the sheath 174. The rotation actuation handles 162*a,b* are disposed proximal of the proximal end 178 of the sheath 174. The needle insert members 192a,b (not shown in FIGS. 16 and 17) are inserted through the working pieces 152a,b with the heads 194a,b engaged with the fluid connection hubs 160a,b of the working pieces 152a,b. FIG. 16 shows the facet joint surgical tool 200 with the rotatable members 158a,b rotated to relative positions where the distal end portions 166a,b are in a facet joint penetration configuration with a piercing tip to pierce though tissue and penetrate into a facet joint as needed for a facet joint surgical procedure. FIG. 17 shows the rotatable members 158a,b rotated to relative positions with the distal end portions 166a,b in a facet joint retraction configuration with the distal tips 154a,b separated by approximately the combined diameters of the rotatable members 158a,b. As shown in FIG. 17, in the facet joint retraction configuration the rotatable members 158a,b have each been rotated 180° relative to positioning shown in FIG. 16 through manipulation of the rotation actuation handles 162a,b, as shown by the rotational arrows in FIG. 17. In either of the configurations shown in FIGS. 16 and 17, the stylets 190a,b may be removed from one or both of the working pieces 152a,b to open the lumen through the respective rotatable member 158a,b to permit access for medical procedures during a surgical operation.

Figure 18:
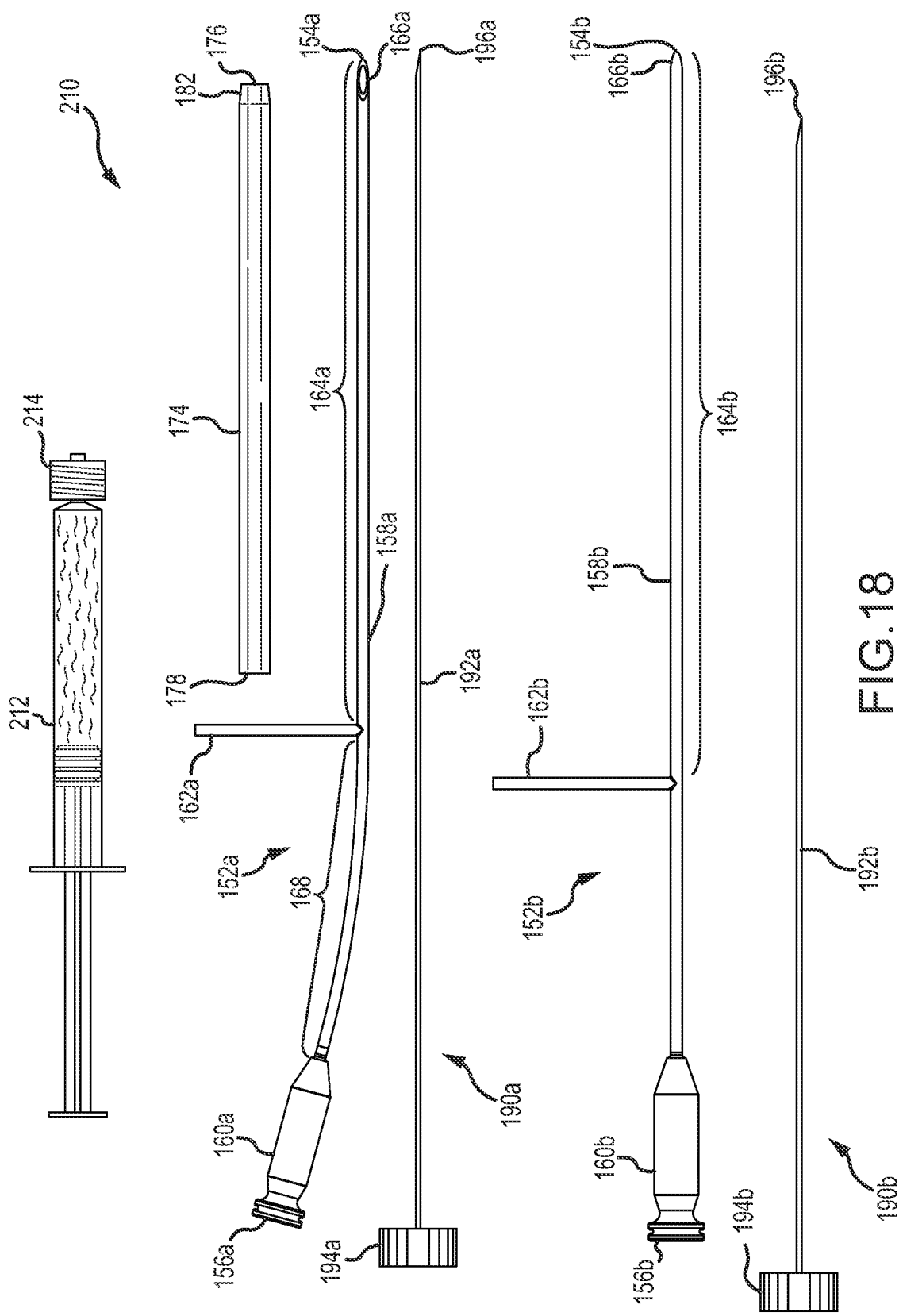
FIG. 18 illustrates another kit and components thereof.
Figure 19:
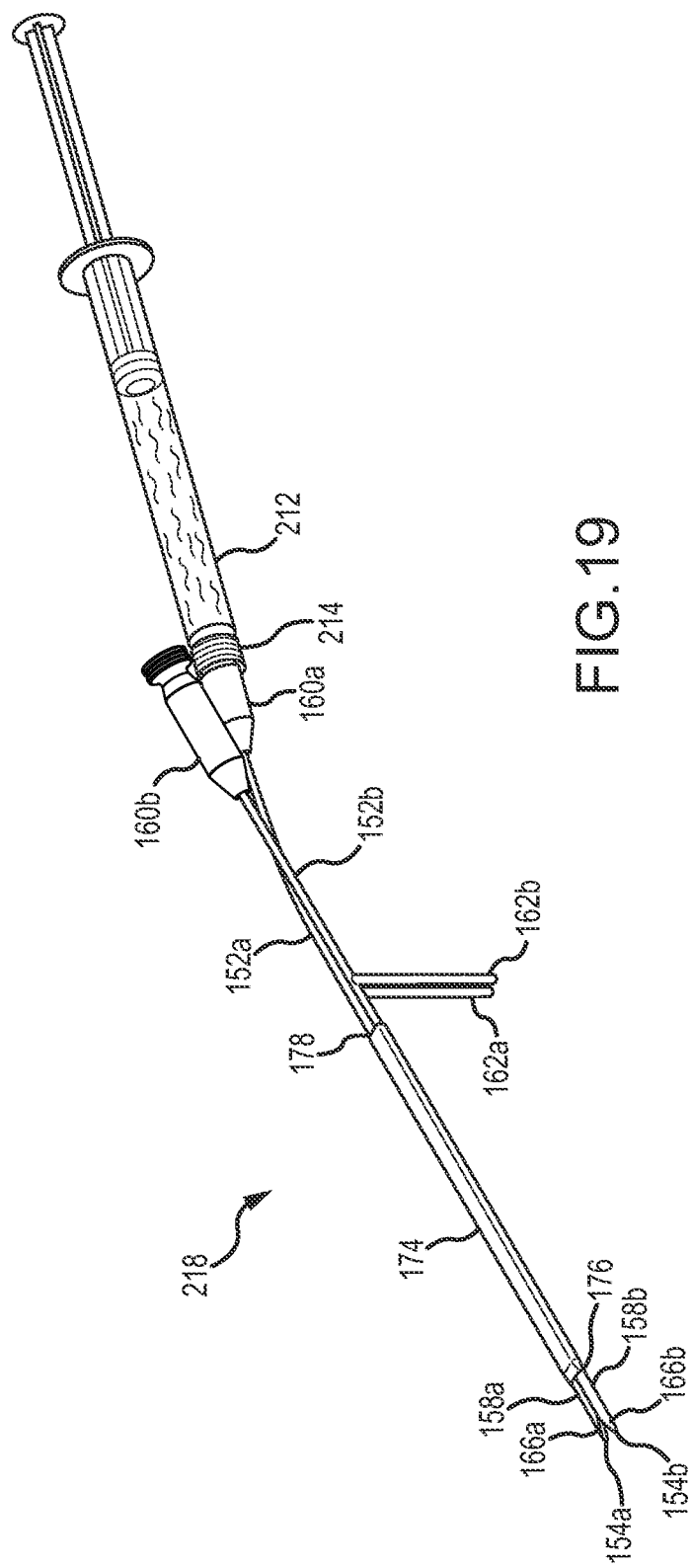
FIG. 19 illustrates an assembled facet joint surgical tool using components of the kit of FIG. 18.

Referring now to FIG. 18, another example kit 210 is shown that includes the working pieces 152a,b, the sheath 174, and the stylets 190a,b shown in FIGS. 12-17. The kit 210 shown in FIG. 18 also includes a fluid manipulation device in the form of a syringe 212, which may be pre-filled with a fluid composition for use during a facet joint synovial cyst surgical operation. The syringe 212 includes a fluid connector 214 configured to engage with an end portion of the fluid connection hubs 160a,b to permit the syringe 212 to be used to manipulate fluid through the lumen of a rotatable member 158. Such a kit 210 may include multiple ones of such a fluid manipulation device as the syringe 212, with different ones of such syringes 212 including different fluid compositions for use during a surgical operation. For example, a syringe 212 may be pre-filled with an irrigation liquid, such as a saline solution, and another such syringe 212 may be pre-filled with a fluid composition including an active component, for example a collagenase or a hyaluronidase, used to treat a facet joint synovial cyst. FIG. 19 illustrates an example facet joint surgical tool 218 including assembled components from the kit 210, including the working pieces 152a,b, sheath 174 and syringe 212. The sylets 190a,b are not included in the assembly of the surgical tool 218. As shown in FIG. 19, the rotatable members 158a,b have relative positioning so that the distal end portions 166a,b are in a facet joint retraction configuration, similar to as shown in FIG. 17, but without the sylets 190a,b received through the working pieces 152a,b and with the syringe 212 fluidly connected with working piece 152a through the fluid connection hub 160a to permit manipulation of fluid by the syringe through the lumen of the rotatable member 158a.

Figure 20:
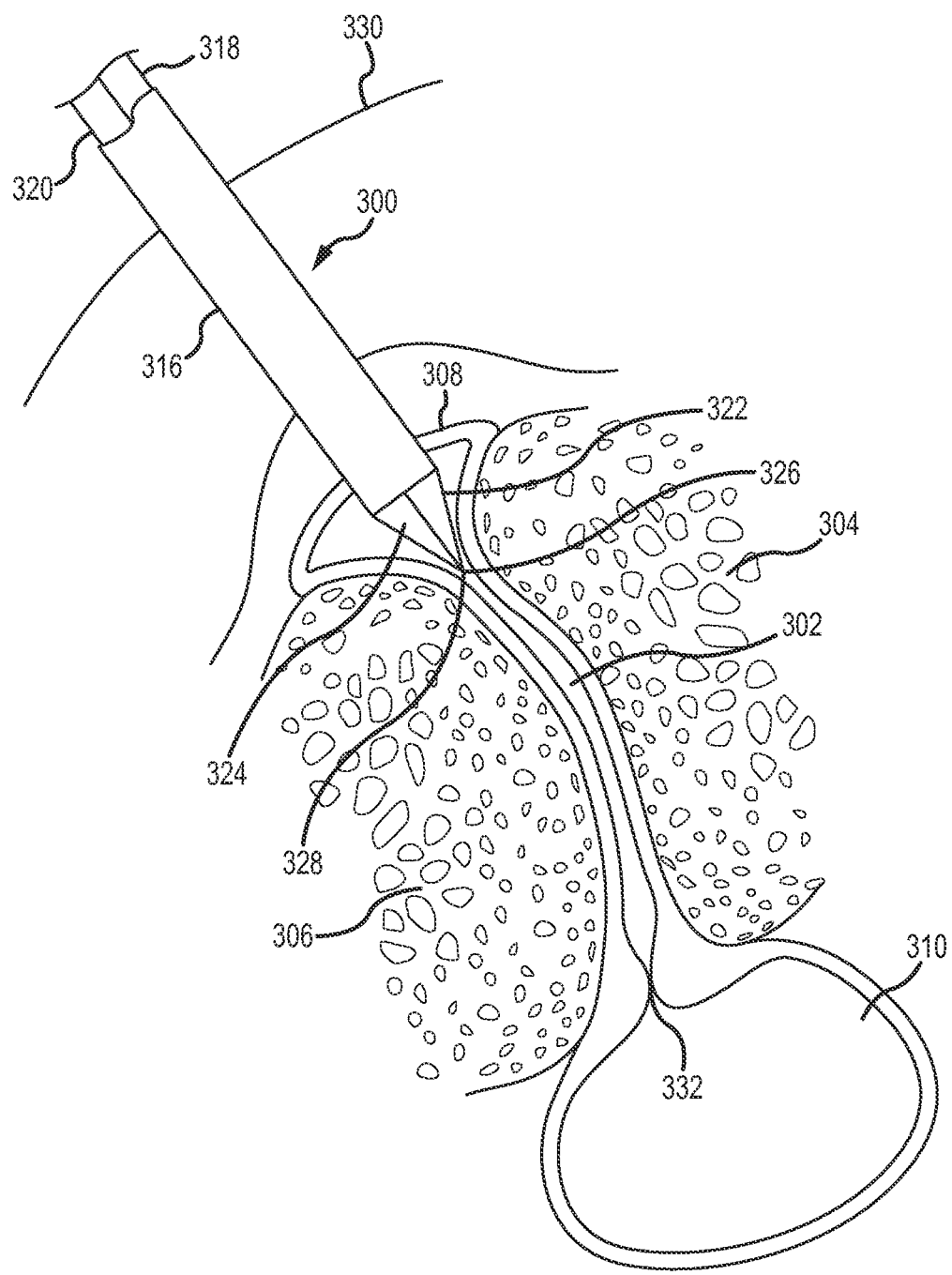
FIGS. 20-28 illustrate use of a facet joint surgical tool to treat from a posterior side a synovial cyst located anterior of a facet joint.

Reference is now made to FIGS. 20-28 illustrating some example surgical procedures using a facet joint surgical tool of this disclosure to treat an anterior facet joint synovial cyst. FIG. 20 shows a portion of a facet joint surgical tool 300 inserted through the skin 330 of a patient through tissue of the patient to a posterior side of a facet joint 302 between a superior articular process 304 and an inferior articular process 306 of adjacent vertebrae. The synovial membrane, or synovium, 308 secretes synovial fluid to lubricate the facet joint 302. A synovial cyst 310 is located to the anterior side of the facet joint 302 and is fluidly connected with the interior of the facet joint 302 through a small opening through a neck 332. For illustration, the synovial cyst 310 is depicted in FIG. 20 as a true cyst lined with synovial cells, but alternatively the synovial cyst 310 could be a pseudocyst formed in tissue anterior to the synovium on the anterior side of the facet joint 302. Shown in FIG. 20 is an inserted portion of the surgical tool 300 including a portion of a sheath 316 having disposed therethrough two rotatable members 318 and 320 with distal end portions 322 and 324 configured to form a piercing tip. As shown in FIG. 20, the piercing tip of the facet joint surgical tool 300 has been advanced to a point where distal tips 326 and 328 of the rotatable members 318 and 320 project into the facet joint 302 from the posterior side. The facet joint surgical tool 300 may, for example, be the facet joint surgical tool 200 configured in the facet joint penetration configuration as shown in FIG. 16, or may be of a different design. In a preferred implementation, when penetrating through tissue to the facet joint 302, the surgical tool 300 may be configured with sylets disposed through lumens of the rotatable members 318 and 320 to close off distal ends of the lumens to prevent tissue coring during tissue penetration.

Figure 21:
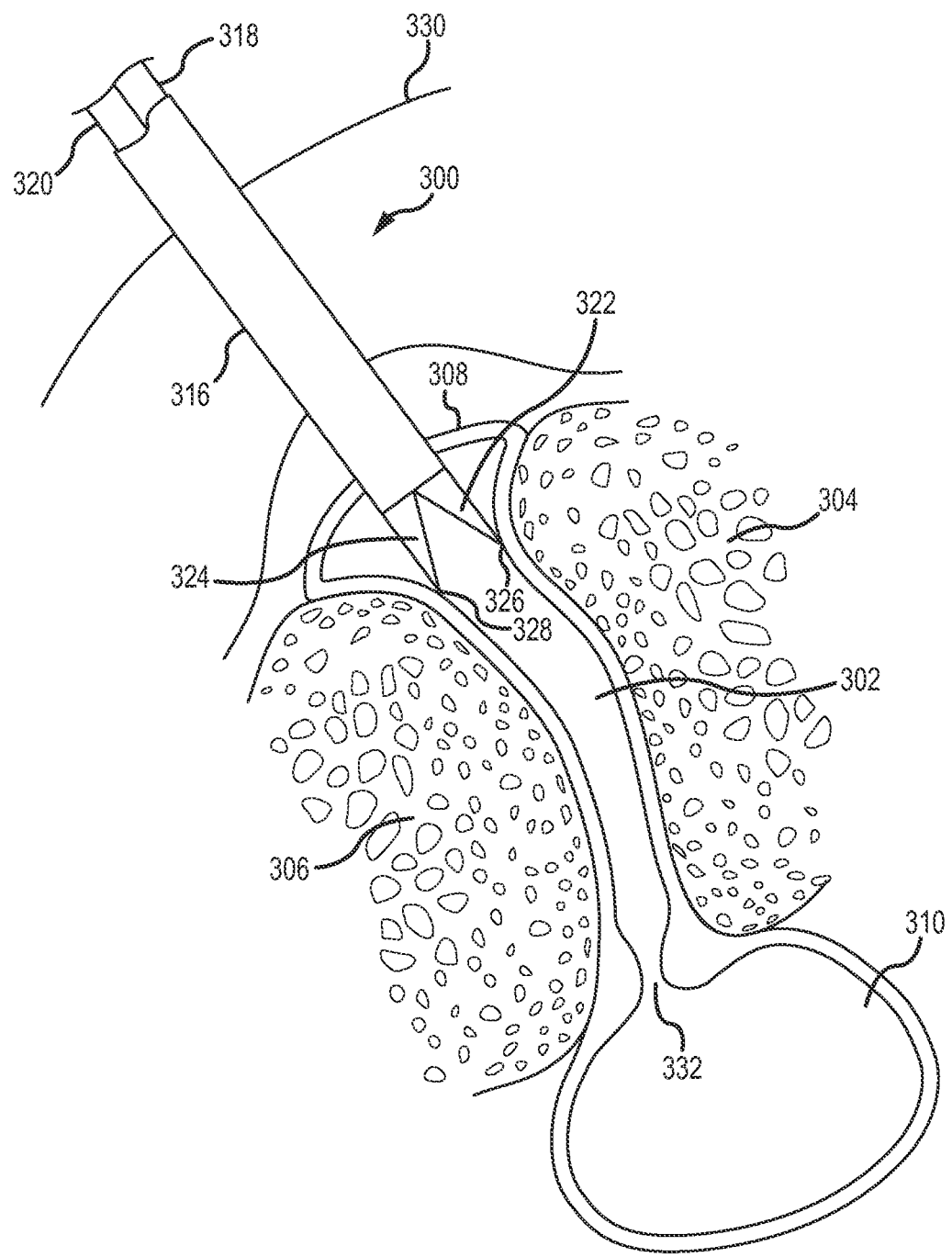

FIG. 21 shows the facet joint surgical tool 300 at the same point of advancement as shown in FIG. 20, except that the rotatable members 318 and 320 have been rotationally repositioned so that the distal end portions 322 and 324 are in a facet joint retraction configuration to retract the facet joint 302, to provide a larger opening through the facet joint 302 for performance of medical procedures directed towards treatment of the synovial cyst 310. The retraction may also help to increase the opening through the neck 332 into the synovial cyst 310. Stylets through lumens of the rotatable members 318 and 320 may be removed before or after rotating the rotatable members 318 and 320 to reconfigure the distal end portions 322 and 324 from the facet joint penetration configuration to the facet joint retraction configuration.

Figure 22:
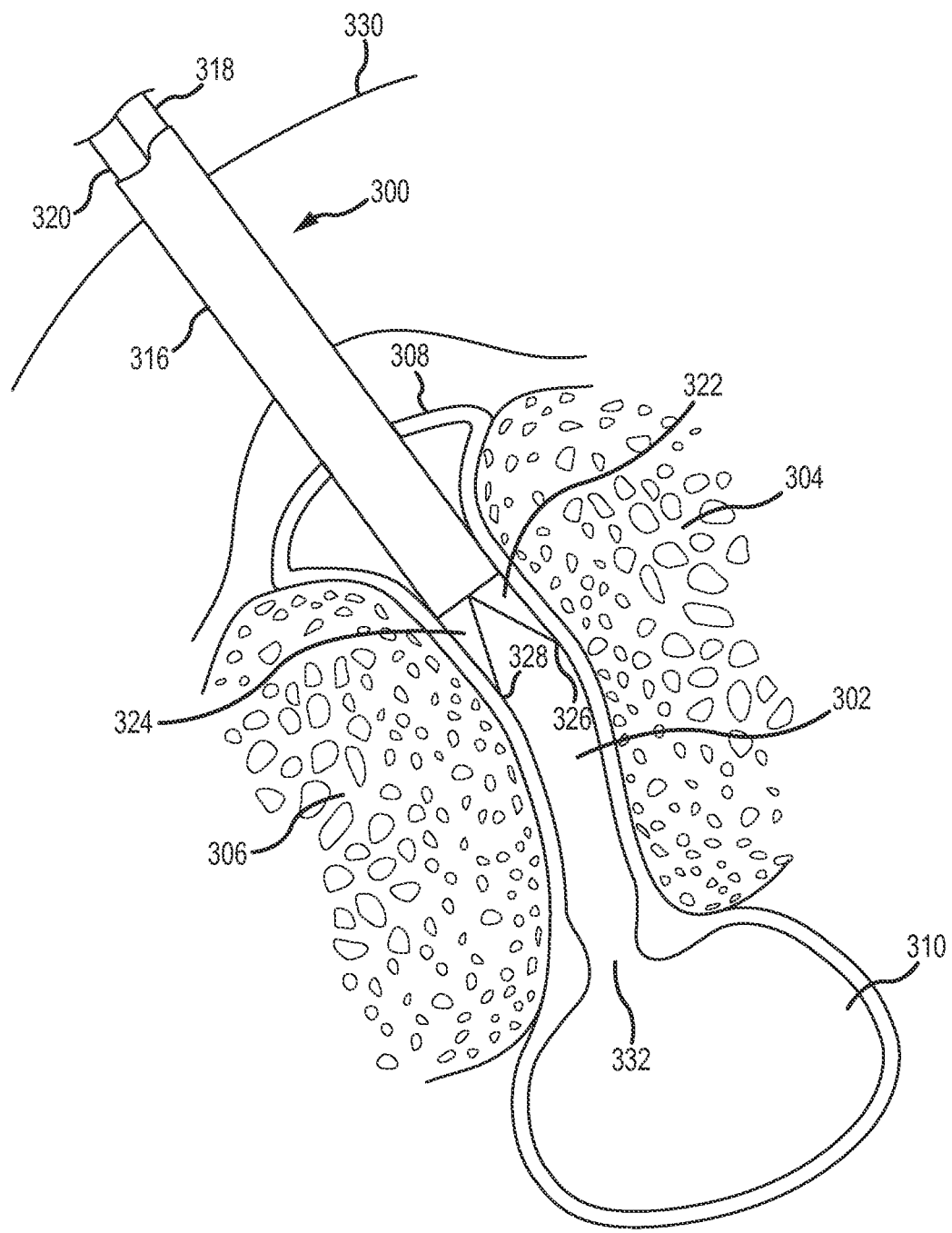
Figure 23:
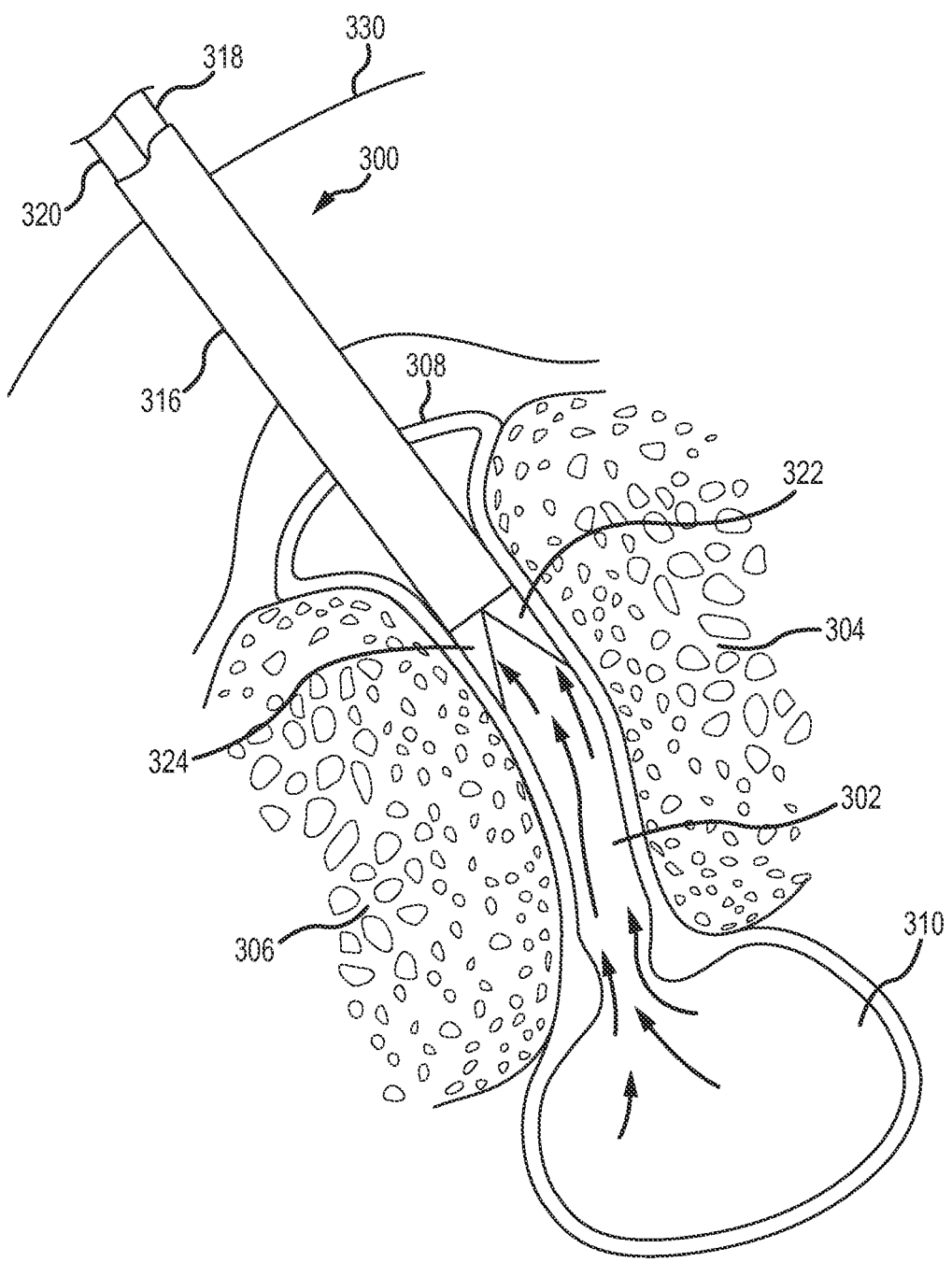

FIG. 22 shows the facet joint surgical tool 300 advanced deeper into the facet joint 302 to a point where the sheath 316 is jammed into the joint to keep the joint open, permitting the rotatable members to be moved, repositioned or removed from the sheath 316 as needed for performing medical procedures while maintaining the facet joint 302 in a retracted position. FIG. 23 shows the facet joint surgical tool 300 in the same positioning as shown in FIG. 22, except with suction being applied through the lumen of one or both of the rotatable member 318 and 320 to aspirate fluid that is amendable to aspiration from the facet joint 302 and the synovial cyst 310. Aspiration is shown with the distal end portions 322 and 324 in the retraction configuration, but such aspiration could also be performed with the distal portions positioned in the piercing configuration or in a different configuration. Because of the highly viscous nature of material in the facet joint 302 and the synovial cyst 310, and the often restricted opening between the two, such aspiration may often not remove a significant amount of fluid or provide enhancement of fluid communication into the facet joint 302 from the synovial cyst 310.

Figure 24:
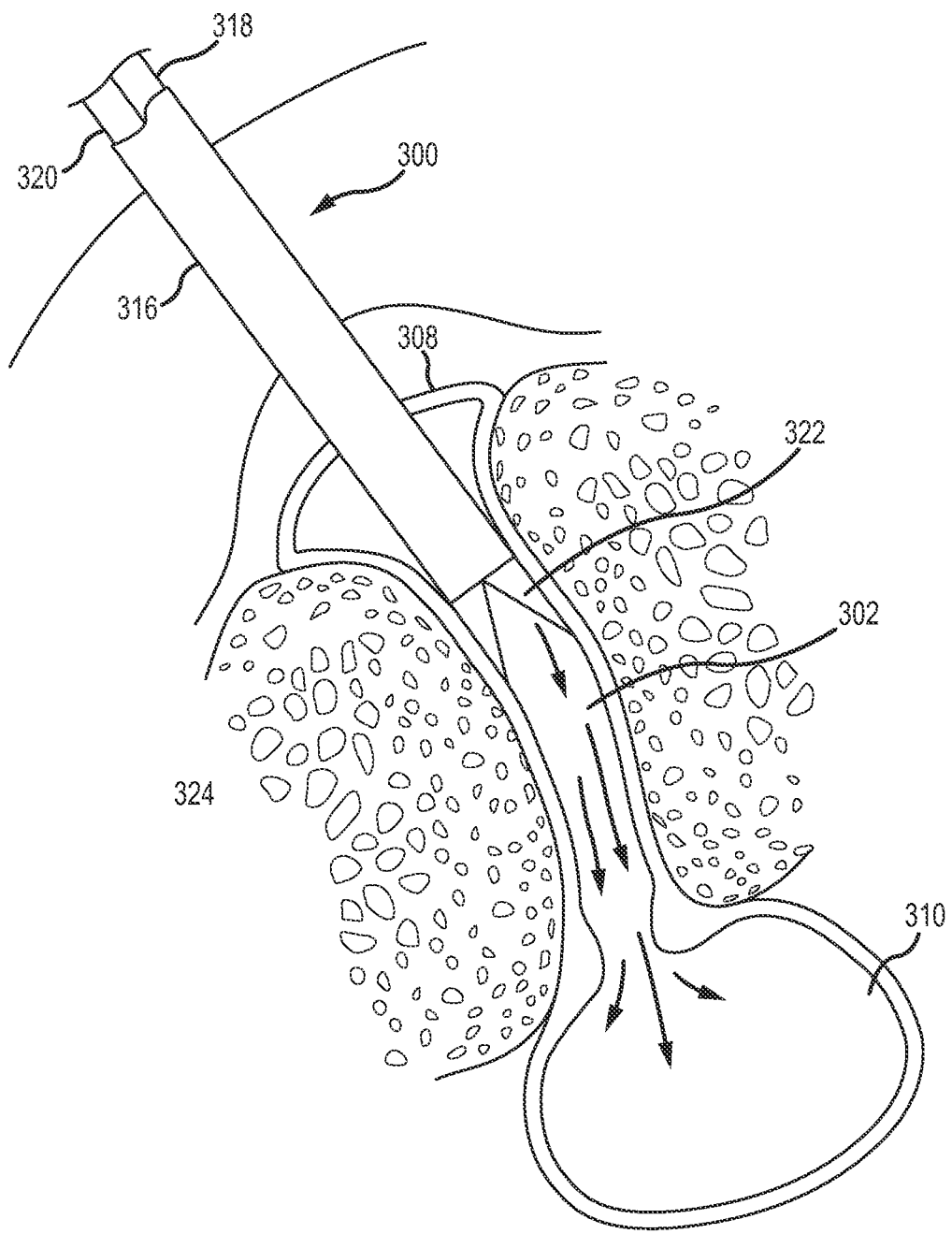

FIG. 24 shows the facet joint surgical tool 300 in the same position as shown in FIGS. 22 and 23, but with a fluid composition being injected into the facet joint 302 through the lumen of one or both of the rotatable members 318 and 320. The fluid composition may include an active component to help liquefy or to decompose tissue within the facet joint 302 and/or the synovial cyst 310, such as for example a hyaluronidase or a collagenase. Fluid pressure from the fluid injection alone or together with liquefying action of an active component in the fluid composition may help to improve fluid communication to the synovial cyst 310. Such fluid pressure may alternatively be provided by injecting irrigation liquid as the fluid composition, for example apply fluid pressure to help increase the fluid opening to the synovial cyst 310 or even to rupture the synovial cyst 310.

Figure 25:
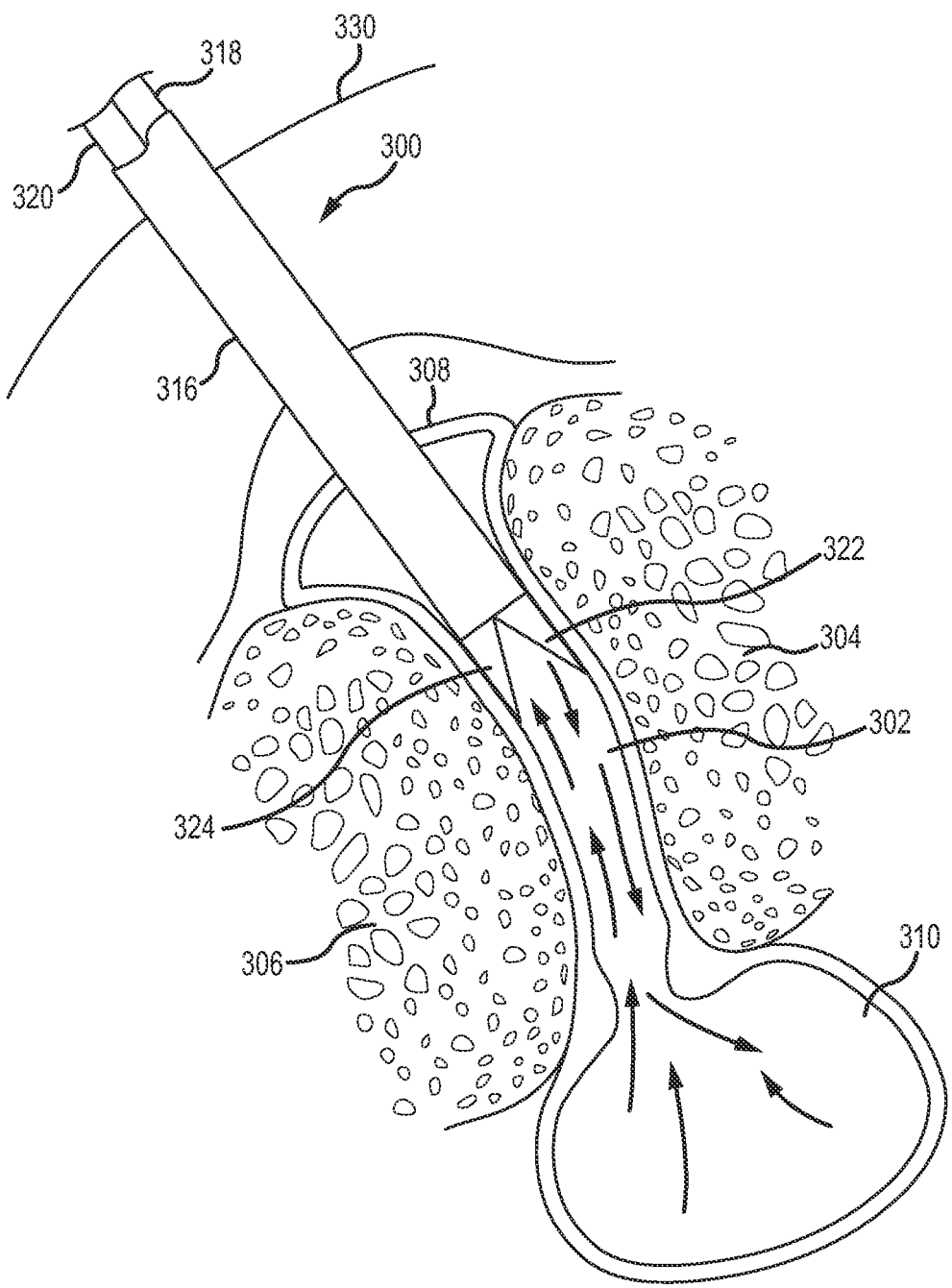

When the fluid composition includes an active component to help liquefy the material within the synovial cyst, the procedure may be discontinued for a wait time to allow the action component time to work before attempting to further remove material from the synovial cyst 302. Following such a wait time after injecting such a fluid composition, the joint may be aspirated, for example in a manner as shown in FIG. 23, to remove liquefied material, either due to viscosity reduction, such as through the addition of hyaluronidase, or through lower viscosity material resulting from digestion of tissue, for example using a collagenase. When using a collagenase, the tissue may alternatively be not aspirated and maybe left to digest and be removed by normal metabolic activity. In addition to or as an alternative to aspiration in a manner as shown in FIG. 23, the facet joint 302 and synovial cyst 310 may be irrigated with an irrigation liquid to help remove tissue from the synovial cyst 310, either before or after injection of a fluid composition such as shown in FIG. 24. In one variation, such an active fluid composition may be injected as shown in FIG. 23 and then after some wait time, the facet joint 302 and synovial cyst 310 may be irrigated with an irrigation liquid as shown in FIG. 25 to help flush reduced viscosity tissue from the synovial cyst 310 for removal through the rotatable member 320 while irrigation liquid is introduced through the other rotatable member 318.

Figure 26:
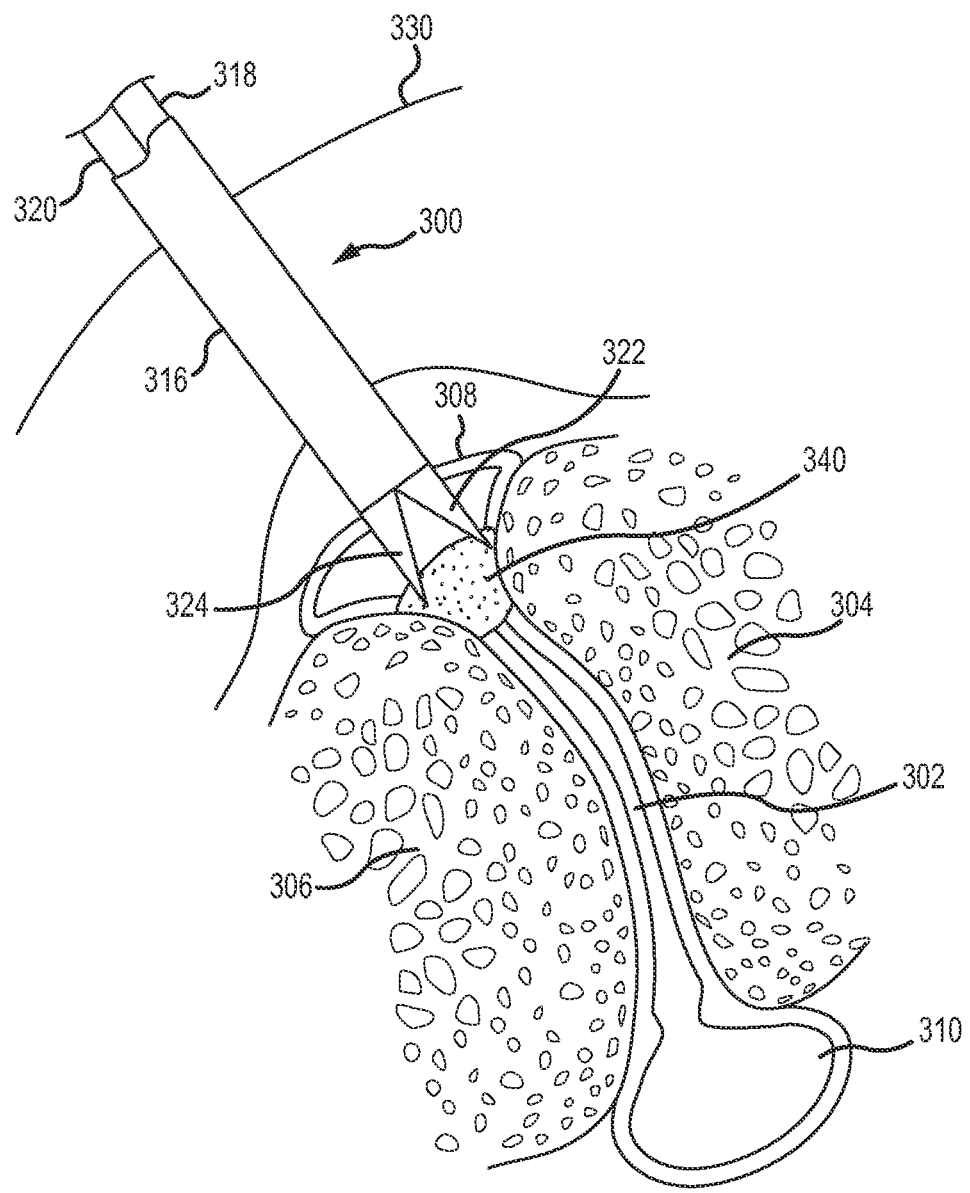

Referring now to FIG. 26, the facet joint surgical tool 300 is shown following treatment of the synovial cyst 310 and showing the synovial cyst 310 significantly reduced in size due to removal of material from the volume of the synovial cyst 310. In FIG. 25, the facet joint surgical tool 300 has been withdrawn to a more posterior position at which one or both of the rotatable members 318 and 320 are used as a RF electrode for performing a RF ablation procedure at the posterior edge of the facet joint 302 to create an artificial cavity. For example, the rotatable members 318 and 320 may be made of a metallic material (e.g., stainless steel) useful for transmitting RF signals. The RF ablation procedure ablates tissue at the posterior edge of the facet joint 302 to create an ablated tissue volume 340 to provide an artificial cavity to provide a volume to receive excess synovial fluid as an alternative to synovial cyst recurrence on the anterior side of the facet joint 302. Following creation of the artificial cavity of the ablated tissue volume 340, the facet joint surgical tool 300 may be further withdrawn from the patient.

Figure 27:
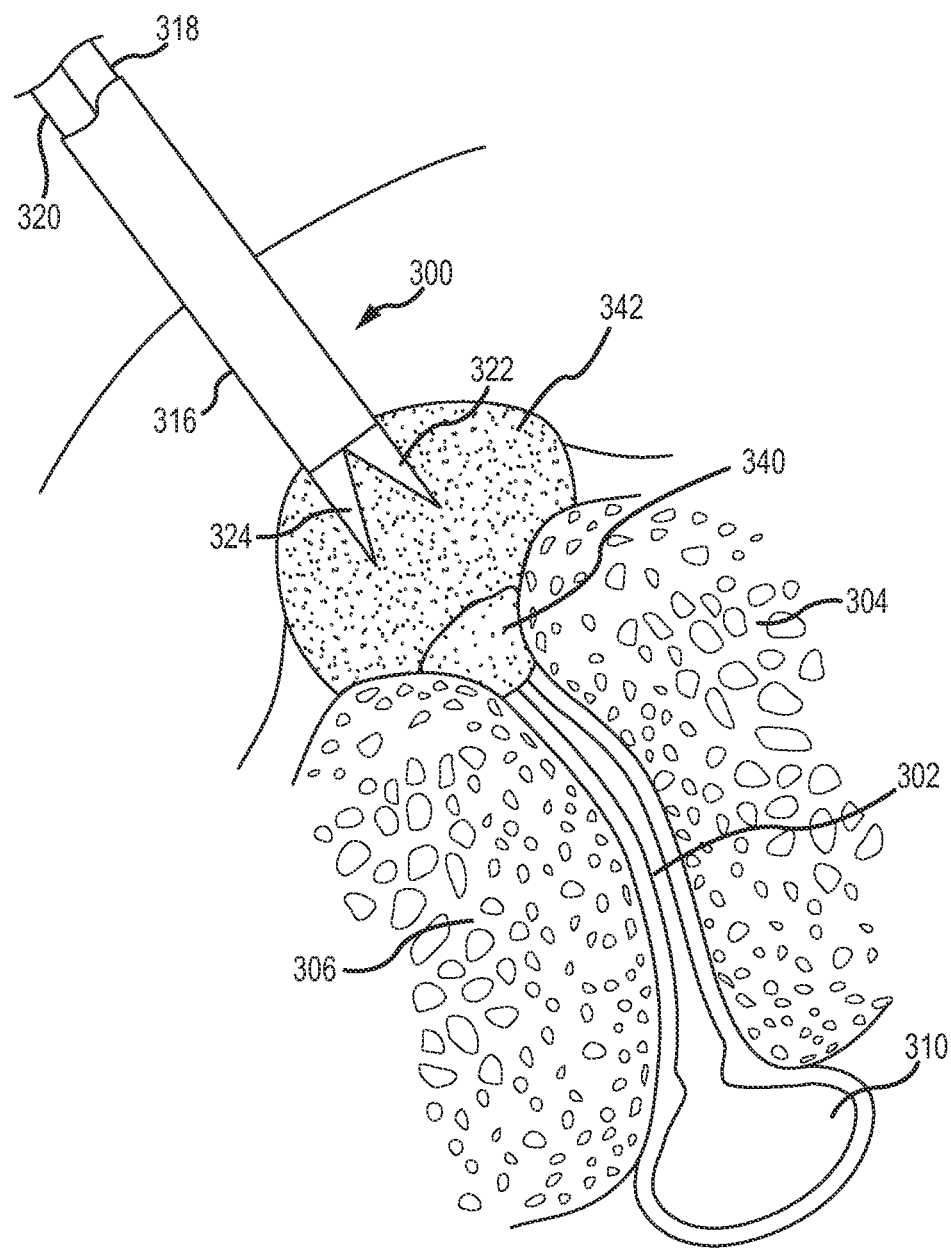
Figure 28:
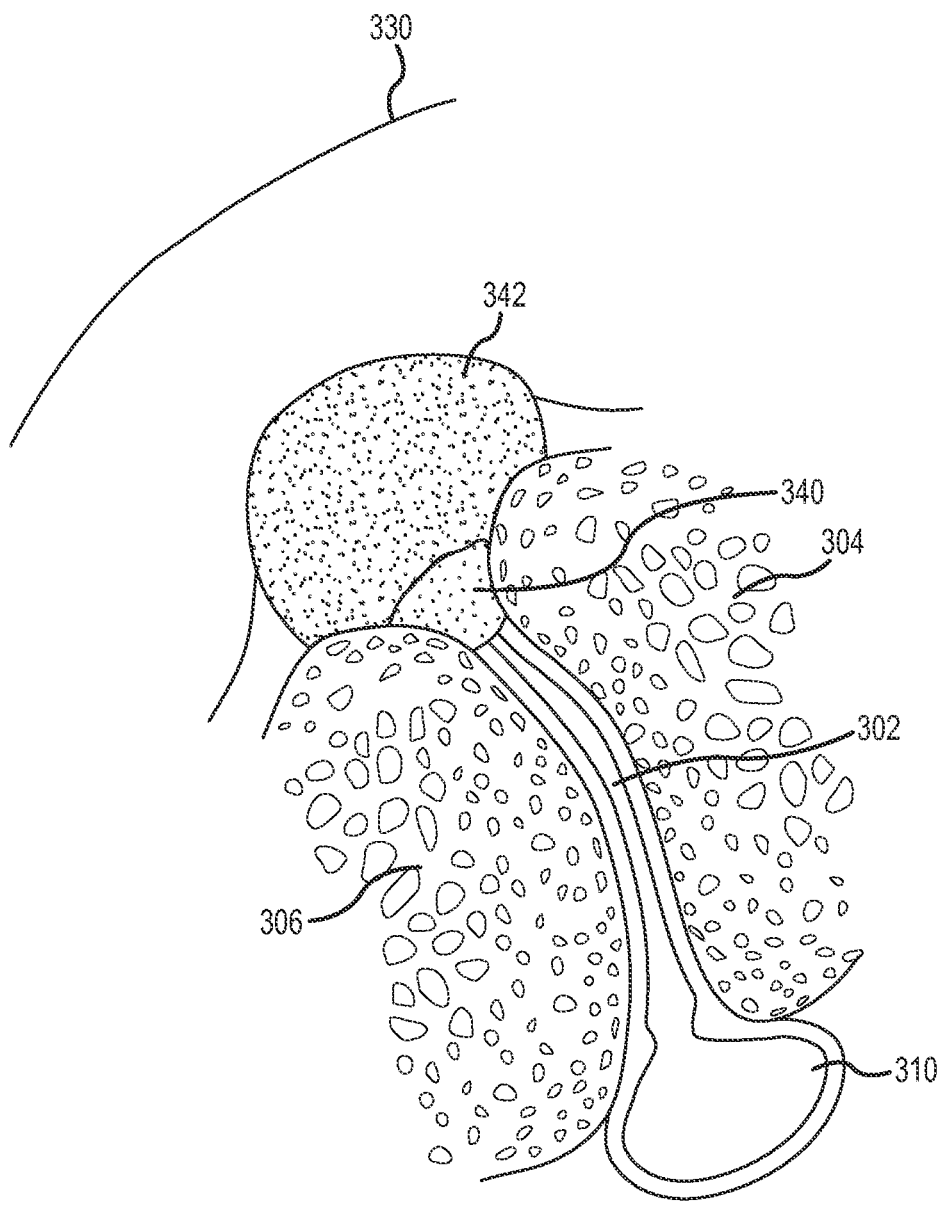

Reference is now made to FIG. 27 in which the facet joint surgical tool 300 has been further withdrawn to a more posterior location relative to the ablated tissue volume 340. At this location, a further tissue ablation procedure may be performed as shown in FIG. 27 to prepare a second ablated tissue volume 342, such as by RF ablation that may again use one or both of the rotatable members 318, and 320 as a RF electrode for transmitting RF energy for the second ablation procedure. This second RF ablation procedure may be targeted to destroy or significantly impair activity of the synovium located on the posterior side of the facet joint 302, to reduce potential for generating synovial fluid that could fill the artificial cavity or that could migrate through the facet joint 302 to the anterior side to promote recurrence of a synovial cyst on the anterior side of the facet joint 302. After performing this second RF tissue ablation procedure, the facet joint surgical tool 300 may be completely withdrawn from the patient, as shown in FIG. 28.

Referring now to FIG. 29, an example is shown of a facet joint surgical tool with one of the rotatable members connected to a RF signal source for use of the rotatable member as a RF electrode for performing a RF ablation procedure. As shown in FIG. 29, a facet joint surgical tool 400 includes two rotatable members 402 and 404 constrained in a side-by-side relationship through a sheath 406. The rotatable member 404 is electrically connected through an electrical connector 408 with a RF signal generator 410 to provide a RF signal to the rotatable member 402 to be transmitted to a distal end of the rotatable member 402 to emit RF energy for RF tissue ablation.

Any feature of any aspect or any embodiment disclosed herein may be combined in any combination with any feature or features of any other aspect(s) or embodiments(s), and may be applied in like manner to treatment of synovial cysts at synovial joints other than the facet joints.

The foregoing discussion of the invention and different aspects thereof has been presented for purposes of illustration and description. The foregoing is not intended to limit the invention to only the form or forms specifically disclosed herein. Consequently, variations and modifications commensurate with the above teachings, and the skill or knowledge of the relevant art, are within the scope of the present invention. The embodiments described hereinabove are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art. Although the description of the invention has included description of one or more possible implementations and certain variations and modifications, other variations and modifications are within the scope of the invention, e.g., as may be within the skill and knowledge of those in the art after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. Furthermore, any feature described or claimed with respect to any disclosed implementation may be combined in any combination with one or more of any other features of any other implementation or implementations, to the extent that the features are not necessarily technically incompatible, and all such combinations are within the scope of the present invention.

The terms "comprising", "containing", "including" and "having", and grammatical variations of those terms, are intended to be inclusive and nonlimiting in that the use of such terms indicates the presence of some condition or feature, but not to the exclusion of the presence also of any other condition or feature. The use of the terms "comprising", "containing", "including" and "having", and grammatical variations of those terms in referring to the presence of one or more components, subcomponents or materials, also include and is intended to disclose the more specific embodiments in which the term "comprising", "containing", "including" or "having" (or the variation of such term) as the case may be, is replaced by any of the narrower terms "consisting essentially of" or "consisting of" or "consisting of only" (or the appropriate grammatical variation of such narrower terms). For example, a statement that some thing "comprises" a stated element or elements is also intended to include and disclose the more specific narrower embodiments of the thing "consisting essentially of" the stated element or elements, and the thing "consisting of" the stated element or elements. Examples of various features have been provided for purposes of illustration, and the terms "example", "for example" and the like indicate illustrative examples that are not limiting and are not to be construed or interpreted as limiting a feature or features to any particular example. The term "at least" followed by a number (e.g., "at least one") means that number or more than that number. The term "at least a portion" means all or a portion that is less than all. The term "at least a part" means all or a part that is less than all.

The features in the drawings are shown for illustration purposes and to generally show relative positioning and interaction, and the features shown are not necessarily to scale and depictions may not be complete in every detail.

What is claimed is:

1. A method for treating a tissue condition in or anterior to a facet joint, the method comprising:
   accessing and retracting the facet joint from a posterior side;
   with the facet joint retracted, performing a medical procedure from the posterior side through the retracted facet joint to treat tissue in or anterior to the facet joint;
   prior to the retracting, penetrating into tissue of a patient with a distal piercing tip of a facet joint surgical tool, the facet joint surgical tool comprising:
      a distal portion insertable into a patient during a surgical procedure;
      a proximal portion to remain outside of a patient during a surgical procedure;
      a first rotatable member comprising a first distal end portion having a first distal tip, the first rotatable member being rotatable about a first axis; and
      a second rotatable member comprising a second distal end portion having a second distal tip, the second rotatable member being rotatable about a second axis that is different than the first axis; and
      the first and second rotatable members being rotatable relative to each other about the first and second axes respectively to manipulate the relative positioning of the first and second distal end portions between a facet joint penetration configuration in which the first and second distal end portions are positioned to form the piercing tip and a facet joint retraction configuration in which the first and second distal end portions are positioned to retract tissue;
   after the penetrating, advancing the piercing tip through tissue of the patient to the posterior side of the facet joint; and
   after the advancing, performing the retracting with the facet joint surgical tool, wherein the retracting comprises rotating the said rotatable members to reposition the said distal tips from the facet joint penetration configuration to the facet joint retraction configuration to retract the facet joint.

2. A method according to claim 1, wherein the medical procedure comprises applying fluid suction to the facet joint or anterior of the facet joint for aspiration of fluid.

3. A method according to claim 2, wherein the medical procedure comprises injecting a fluid composition into the facet joint to apply fluid pressure to tissue to be treated.

4. A method according to claim 3, wherein the tissue condition comprises a synovial cyst and the method comprises during the injecting fluid, rupturing the synovial cyst.

5. A method according to claim 1, wherein tissue condition comprises a synovial cyst and the medical procedure comprises injecting a fluid composition into the facet joint or directly into the synovial cyst, wherein the fluid composition comprises at least one component to liquefy or decompose tissue within the synovial cyst.

6. A method according to claim 5, wherein the at least one component comprises a hyaluronidase.

7. A method according to claim 5, wherein the at least one component comprises a collagenase.

8. A method according to claim 5, comprising after the injecting, removing liquid from the facet joint or directly from the synovial cyst.

9. A method according to claim 8, wherein the removing liquid comprises irrigating the facet joint with an aqueous irrigation liquid provided to the facet joint.

10. A method according to claim 1, comprising after performing the medical procedure, performing a tissue ablation to ablate at least a portion of synovium at the posterior side of the facet joint.

11. A method according to claim 10, wherein the tissue ablation comprises RF ablation.

12. A method according to claim 1, comprising forming an artificial cavity in or adjacent to the posterior side of the facet joint to provide a volume for collection of synovial fluid as an alternative to collection on the anterior side of the facet joint.

13. A method according to claim 1, wherein each said rotatable member has a lumen to provide access from outside of the patient to inside of the patient, the lumen having a distal end adjacent the distal tip of the said rotatable member;
   during the penetrating, the facet joint surgical tool comprises a stylet disposed through each said lumen with a distal end of a said stylet blocking a distal end of the corresponding lumen adjacent the piercing tip; and
   after the advancing, removing the stylets from the lumens.

14. A method according to claim 1, comprising after the rotating, advancing a sheath over the first rotatable member and the second rotatable member to retract the facet joint with the sheath.

15. A method according to claim 14, comprising, with the facet joint retracted by the sheath:
   removing at least one of the said rotatable members from an internal passage of the sheath; and
   with the at least one of the said rotatable members removed from the internal passage, advancing an insertable surgical tool from outside of the patient through the internal passage of the sheath and out a distal end of the internal passage into the retracted facet joint.

16. A method according to claim 1, wherein the tissue condition comprises a synovial cyst anterior to the facet joint and the method comprises performing the medical procedure to treat the synovial cyst.

17. A method according to claim 1, wherein the medical procedure comprises treating a facet joint synovial cyst, wherein the treating comprises introducing into tissue of the synovial cyst a fluid composition including at least one component to decompose or liquefy the tissue.

18. A method according to claim 17, wherein the at least one component is selected from the group consisting of hyaluronidase and collagenase.

19. A method according to claim 18, comprising after the introducing, removing tissue from the synovial cyst.

* * * * *